(12) United States Patent
Yue et al.

(10) Patent No.: US 6,201,106 B1
(45) Date of Patent: Mar. 13, 2001

(54) CYTOKINE SIGNAL REGULATORS

(75) Inventors: Henry Yue, Sunnyvale; Neil C. Corley, Mountain View; Karl J. Guegler, Menlo Park; Mariah R. Baughn, San Leandro, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/382,086

(22) Filed: Aug. 24, 1999

Related U.S. Application Data

(62) Division of application No. 09/189,035, filed on Nov. 10, 1998, now Pat. No. 6,020,165.

(51) Int. Cl.[7] .......................... C07K 1/00; C07K 14/475; A61K 38/00; A61K 38/16
(52) U.S. Cl. ............................................. 530/350; 514/12
(58) Field of Search ................................ 530/350; 514/12

(56) References Cited

PUBLICATIONS

Charbonneau, H. and Tonks, N.K., "1002 Protein Phosphatases?", *Annu. Rev. Cell Biol.* 8: 463–93 (1992).

Provenzano, C. et al., "Eps8, a Tyrosine Kinase Substrate, Is Recruited to the Cell Cortex and Dynamic F–Actin upon Cytoskeleton Remodeling", *Exp. Cell Res.* 242: 186–200 (1998).

Ziemnicka–Kotula, D. et al., "Identification of a Candidate Human Spectrin Src Homology 3 Domain–binding Protein Suggests a General Mechanism of Association of Tyrosine Kinases with the Spectrin–based Membrane Skeleton*", *J. Biol. Chem.* 273 (22): 13681–13692 (1998).

Kharitonenkov, A. et al., "A family of proteins that inhibit signalling through tyrosine kinase receptors", *Nature* 386: 181–186 (1997).

Biesova, Z. et al., (Direct Submission), GenBank Sequence Database (Accession 2245671), National Center for Biotechnology Information, National Library of Medicine, Bethesda, Maryland, 20894 (GI 2245671), Jul. 2, 1997.

Kharitonenkov, A. et al., (Direct Submission), GenBank Sequence Database (Accession 2052058), National Center for Biotechnology Information, National Library of Medicine, Bethesda, Maryland, 20894 (GI 2052058), May 14, 1997.

National Cancer Institute, Cancer Genome Anatomy Project (CGAP): "np33f08.s1 NCI–CGAP–Lu1 Homo Sapiens cDNA clone IMAGE: 1118151 3 similar to TR:O915311 G915311 ABL INTERACTOR 2, "EMBL DATABASE ENTRY AA622957, ACCESSION NUMBER AA622957, 16 October 1977 (1997–10–16), XP002136504 (99, 8 identity with seq id 3 IN 466 BP overlap between NT1910–1455) abstract & UNPUBLISHED.

*Primary Examiner*—Rebecca E. Prouty
*Assistant Examiner*—Maryam Monshipouri
(74) *Attorney, Agent, or Firm*—Incyte Genomics, Inc.

(57) ABSTRACT

The invention provides human cytokine signal regulators (CKSR) and polynucleotides which identify and encode CKSR. The invention also provides expression vectors, host cells, antibodies, agonists, and antagonists. The invention also provides methods for diagnosing, treating, or preventing disorders associated with expression of CKSR.

4 Claims, 15 Drawing Sheets

```
                    11           20           29           38           47        56
5' CCACC TCC ATC TTC AAC AGG TCC TTC TCG CTG AGA TCC TGG GCC ATC CTG CCC TAG 65           74           83           92          101       110
   ACA GAC CTG ATC CTG CCA CAG AAG ACA AGC ACA CTC TCC AAG TCA CTT GTC CTG GAC 119          128          137          146          155       164
   TCA GGT AAG ATA GTG TTT GAG CCT AGT TCT TCA TCA GCT GAA AAT CTT CAG 173          182          191          200          209       218
   ATA AAG CAG ATG GCC AGT TTC CTC TCC AGG ACC AGG GAG CAA TCA CAG CTG CCC
                    M   A   S   F   L   S   R   T   R   E   Q   S   Q   L   P 227          236          245          254          263       272
   CGA CCT TGG CTT CCT CTG CTG GGT ATT GGG GGC TGG GCC CCC AAA TGG GCC
    R   P   W   L   P   L   L   G   I   G   G   W   A   P   K   W   A 281          290          299          308          317       326
   CCT GGC TTC CCC CTT CCT CTG GGC AGG GGA CAG AGA GAC ACA GGC TCG GGG AGC
    P   G   F   P   L   P   L   G   R   G   Q   R   D   T   G   S   G   S 335          344          353          362          371       380
   AGG ACT GAC TTC CTC TTG TCC CGG AAT GAG CAT GCC TGC CCT TTG CAA GCA GGT
    R   T   D   F   L   L   S   R   N   E   H   A   C   P   L   Q   A   G
```

FIGURE 1A

```
        389         398         407         416         425         434
TTG GGT CTC ACG CAG AGG AAA CCA AAA GCA ATA AGA GGG AGG GAA GGC AGA GCA
 L   G   L   T   Q   R   K   P   K   A   I   R   G   R   E   G   R   A 443         452         461         470         479         488
ACC AAT CAA GGG CAG GGT GAG ACT CAA AAC GAG CGG GCT CCC TGG GGA GCC AGA
 T   N   Q   G   Q   G   E   T   Q   N   E   R   A   P   W   G   A   R 497         506         515         524         533         542
CAG AGG CTG GGG GTG ATG GCG GAG CTA CAG CAG CTG CAG GAG TTT GAG ATC CCC
 Q   R   L   G   V   M   A   E   L   Q   Q   L   Q   E   F   E   I   P 551         560         569         578         587         596
ACT GGC CGG GAG GCT CTG AGG GGC AAC CAC AGT GCC CTG CTG CGG GTC GCT GAC
 T   G   R   E   A   L   R   G   N   H   S   A   L   L   R   V   A   D 605         614         623         632         641         650
TAC TGC GAG GAC AAC TAT GTG CAG GCC ACA GAC AAG CGG AAG GCG CTG GAG GAG
 Y   C   E   D   N   Y   V   Q   A   T   D   K   R   K   A   L   E   E 659         668         677         686         695         704
ACC ATG GCC TTC ACT ACC CAG GCA CTG GCC AGC CAG GTG GCC TAC CAG GTG GGC AAC
 T   M   A   F   T   T   Q   A   L   A   S   Q   V   A   Y   Q   V   G   N
```

FIGURE 1B

```
       713                 722                 731              740                 749                 758
CTG GCC GGG CAC ACT CTG CGC ATG TTG GAC CTG CAG GGG GCC GCC CTG CGG CAG
 L   A   G   H   T   L   R   M   L   D   L   Q   G   A   A   L   R   Q 767                 776                 785              794                 803                 812
GTG GAA GCC CGT GTA AGC ACG CTG GGC CAG ATG GTG AAC ATG CAT ATG GAG AAG
 V   E   A   R   V   S   T   L   G   Q   M   V   N   M   H   M   E   K 821                 830                 839              848                 857                 866
GTG GCC CGA AGG GAG ATC GGC ACC TTA GCC ACT GTC CAG CGG CTG CCC CCC GGC
 V   A   R   R   E   I   G   T   L   A   T   V   Q   R   L   P   P   G 875                 884                 893              902                 911                 920
CAG AAG GTC ATC GCC CCA GAG AAC CTA CCC CTC ACG CCC TAC TGC AGG AGA
 Q   K   V   I   A   P   E   N   L   P   L   T   P   Y   C   R   R 929                 938                 947              956                 965                 974
CCC CTC AAC TTT GGC TGC CTG GAC GAC ATT GGC CAT GGG ATC AAG GAC CTC AGC
 P   L   N   F   G   C   L   D   D   I   G   H   G   I   K   D   L   S 983                 992                 1001             1010                1019                1028
ACG CAG CTG TCA AGA ACA GGC ACC CTG TCT CGA AAG AGC ATC AAG GCC CCT GCC
 T   Q   L   S   R   T   G   T   L   S   R   K   S   I   K   A   P   A
```

FIGURE 1C

```
      1037            1046            1055            1064            1073            1082
ACA   CCC   GCC   TCC   GCC   ACC   TTG   GGG   AGA   CCA   CCC   GAG   CCA   GTG   CAC
 T     P     A     S     A     T     L     G     R     P     P     E     P     V     H 1091            1100            1109            1118            1127            1136
CTG   CCG   GTG   GTG   CCC   GAC   GGC   AGA   CTC   TCC   GCC   GCC   ATT   CCC   TCT   TCC   CTG
 L     P     V     V     P     D     G     R     L     S     A     A     I     P     S     S     L 1145            1154            1163            1172            1181            1190
GCC   TCG   GGC   AGC   GCC   GAA   GGT   GTC   GGG   CCC   ACG   CCC   AAG   GGG   CAG
 A     S     G     S     A     E     G     V     G     P     T     P     K     G     Q 1199            1208            1217            1226            1235            1244
GCA   GCC   CCT   CCA   GCC   CCA   CCT   CTC   CCC   AGC   TCC   TTG   GAC   CCA   CCT   CCA   CCA
 A     A     P     P     A     P     P     L     P     S     S     L     D     P     P     P     P 1253            1262            1271            1280            1289            1298
GCC   GTC   GAG   GTG   TTC   CAG   CGG   CCA   CCT   CCC   ACG   CTG   GAG   GAG   TTG   TCC   CCA   CCC
 A     V     E     V     F     Q     R     P     P     P     T     L     E     E     L     S     P     P 1307            1316            1325            1334            1343            1352
GCA   GCC   GAC   GAA   GAG   CTG   CCC   CCA   CCA   CTG   CCC   CCT   CCT   CCA   CCA   CCC   CTG
 A     A     D     E     E     L     P     P     P     L     P     P     P     P     P     P     L
```

FIGURE 1D

```
      1361           1370           1379           1388           1397          1406
GAT GGA GAT GAA TTG GGG CTG CCT CCA CCC CCA GGA TTT GGG CCT GAT GAG
 D   G   D   E   L   G   L   P   P   P   P   G   F   G   P   D   E 1415           1424           1433           1442           1451          1460
CCC AGC TGG GTG CCT GCC TCA TAC TTG GAG AAA GTG GTG ACA CTG TAC CCA TAC
 P   S   W   V   P   A   S   Y   L   E   K   V   V   T   L   Y   P   Y 1469           1478           1487           1496           1505          1514
ACC AGC CAG AAG GAC AAT GAG CTC TCC TTC TCT GAG GGC ACT GTC ATC TGT GTC
 T   S   Q   K   D   N   E   L   S   F   S   E   G   T   V   I   C   V 1523           1532           1541           1550           1559          1568
ACT CGC TAC TCC GAT GGC TGG TGC GAG GGC GTC AGC TCA GAG GGG ACT GGA
 T   R   Y   S   D   G   W   C   E   G   V   S   S   E   G   T   G 1577           1586           1595           1604           1613          1622
TTC TTC CCT GGG AAC TAT GTG GAG CCC AGC TGC TGA CAG CCC AGG GCT CTC TGG
 F   F   P   G   N   Y   V   E   P   S   C   *   Q   P   R   A   L   W 1631           1640           1649           1658           1667          1676
GCA GCT GAT GTC TGC ACT GAG TGG GTT TCA TGA GCC CCA AGC CAA AAC CAG CTC
 A   A   D   V   C   T   E   W   V   S   *   A   P   S   Q   N   Q   L
```

FIGURE 1E

```
        1685      1694      1703      1712      1721      1730
        CAG TCA CAG CTG GAC GTC TGC CCA CCT CTT GGG CTG TGA GCT GTG TTC TGT 1739      1748      1757      1766      1775      1784
        CCT TCC TCC CAT CGG AGG GAG AAG GGG TCC TGG GGA GAG AGA ATT TAT CCA GAG 1793      1802      1811      1820      1829      1838
        GCC TGC TGC AGA TGG GGA AGA GCT GGA AAC CAA GAA GTT TGT CAA CAG AGG ACC 1847      1856      1865      1874      1883      1892
        CCT ACT CCA TGC AGG ACA GGG TCT CCT GCT GCA AGT CCC AAC TTT GAA TAA AAC 1901      1910      1919      1928      1937      1946
        AGA TGA TGT CCT GTG ACT GCC CCA CAG AGA TAA GGG GCC AGG AGG GAT TGA AAG 1955      1964      1973      1982      1991      2000
        GCA TCC CAG TTC TAA GGC TGC TGC TAA TTA CAG CCC CCA ACC TCC AAC CCA CCA
```

FIGURE 1F

```
     2009        2018         2027        2036        2045      2054
GCT GAC CTA GAA GCA GCA TCT TCC CAT TTC CTC AGT ACC CAC AAA GTG CAG CCC 2063        2072         2081        2090        2099      2108
ACA TTG GAC CCC AGA CAC CCC TCT GCA GCC ATT GAC TGC AAC TTG TTC TTT TGC 2117        2126         2135        2144        2153      2162
CCA TTG CTT GCT GTG TGT GTG GTG TCA TAT GTG GCT GGG CAC TTG CCC AAG 2171        2180         2189        2198        2207      2216
AGT GGG AAC GAT CTC CAT GAC TTA AGC GGG GCT CTC CGA GAG CAC CTC ACT GTC 2225        2234         2243        2252        2261      2270
AAC TCT GAG ACT GTC GCG AGA GAG ATC TCA GTC ATT TCT TCC CCC TTC ACC TCC 2279        2288
TTT ATA GTT GTA AAA CTC CAG AGG A 3'
```

FIGURE 1G

```
                                                                56
5' CAGAG CAG GCT TCT GAG GTC TCC AAA ATG CCT GTC CCA GCC TCC TGG CCC CAT CCT
                                     11        20            29            38            47
                                                M   P   V   P   A   S   W   P   H   P 65             74            83            92           101           110
CCT GAT CCT TTC CTG CTT CTG ACT CTA CTG CTG GGA CTT ACA GAA GTG GCA GGT
 P   D   P   F   L   L   L   T   L   L   L   G   L   T   E   V   A   G 119           128           137           146           155           164
GAG GAG CTA CAG ATG ATT CAG CCT GAG AAG CTC CTG TTG GTC ACA GTT GGA
 E   E   L   Q   M   I   Q   P   E   K   L   L   L   V   T   V   G 173           182           191           200           209           218
AAG ACA GCC ACT CTG CAC TGC ACT GTG ACC TCC CTG CTT CCC GGA CCC GTC
 K   T   A   T   L   H   C   T   V   T   S   L   L   P   G   P   V 227           236           245           254           263           272
CTG TGG TTC AGA GGA GTT GGA CCA GGC CGA GAA CTG CTT AAT CAA AAA GAA
 L   W   F   R   G   V   G   P   G   R   E   L   L   N   Q   K   E 281           290           299           308           317           326
GGC CAC TTC CCC AGG GTA ACA ACA GTT TCA GAC CTC ACA AAG AGA AAC AAC ATG
 G   H   F   P   R   V   T   T   V   S   D   L   T   K   R   N   N   M 335           344           353           362           371           380
GAC TTT TCC ATC CGC ATC AGT AGC ATC ACC CCA GCA GAT GTC GGC ACA TAC TAC
 D   F   S   I   R   I   S   S   I   T   P   A   D   V   G   T   Y   Y
```

FIGURE 2A

```
          389              398              407              416              425              434
TGT GTG AAG TTT CGA AAA GGG AGC CCT GAG AAC GTG GAG TTT AAG TCT GGA CCA
 C   V   K   F   R   K   G   S   P   E   N   V   E   F   K   S   G   P 443              452              461              470              479              488
GGC ACT GAG ATG GCT CTC TTG GGT GGC CCG GCA TCA TCC CTT ACT GCG CTG CTC
 G   T   E   M   A   L   L   G   G   P   A   S   S   L   T   A   L   L 497              506              515              524              533              542
ATA GCT GTC CTC CTG GGC CCC ATC TAC GTC CCC TGG AAG CAG AAG ACC TGA CTC
 I   A   V   L   L   G   P   I   Y   V   P   W   K   Q   K   T   *

551              560              569              578              587              596
TCC TTC CTT CCT CCC CTG CCA CGT GGG ACC CTC ATC TCT GCT GCC TCC TTC CTT 605              614              623              632              641              650
TCC TGA GAG GCT CTT GAG AGA ATG AGC CAG TGA GAA GCT TCT CTA GAC TTG 659              668              677              686              695              704
GCT CCA AAC ATC TCC CCT CCC AAG ACA TCT GCC TGC CCA CAG GCT CCT GTT GCT
```

FIGURE 2B

```
       713         722         731         740         749         758
CCT TCA CAC AGA CCT GGA TGC CCC AGA GCA AGG TCT TCA TTC ATG GTC CTG AGC 767         776         785         794         803         812
AGG TGC CAT GGG ATT GGG CTC TGG GCA CTG ACT TAA CGG CAC CTC CCT AGA AGG 821         830         839         848         857         866
CGA GAA ACA TGC CAA ATC TAA ACA CAC CAG GAC TCC CAT CCA TCG CCT TGA GAC 875         884         893         902         911         920
TGA CCG TAA ACC ACA GAC GCT CTC CAG GTT CTC AAG AGT TAT CCT GCC TTC CAG 929         938         947         956         965         974
ATT CCT GCC TAT CCC AAC TCC CCA GCC TTG TTG AGG TTC TCT ATT GCC TCT TGA 983         992        1001        1010        1019
ATA CAA ATG CAC TCC CAA AGT GGT TTT AAG AAA ATA AAA AGA TTA TCC  3'
```

```
211  MEKVARREIGTLATVQRLPPGQKVIAPENL                          2280326
101  KEKVARREIGILTTNKNTSRTHKIIAPANM                          GI 2245671

241  PPLTPYCRRPLNFGCLDDIGHGIKDLST--                          2280326
131  ERPVRYIRKPIDYTVLDDVGHGVKWLKAKH                          GI 2245671

269  ---QLSRTGTLSRKSI--KAPATPASA---                          2280326
161  GNNQPARTGTLSRTNPPTQKPPSPPMSGRG                          GI 2245671

291  TLGR--PPRIPEPVHLPVVPDGRLSAASSA                          2280326
191  TLGRNTPYKTLEPVKPPTVPNDYMTSPARL                          GI 2245671

319  SSLASAGSAE---------GVGGAPTPKG                           2280326
221  GSQHSPGRTASLNQRPRTHSGSSGGSGSRE                          GI 2245671

339  QAAPPAPPLPSSLDPPPPA-----------                          2280326
251  NSGSSSIGIPIAVPTPSPPTIGPAPGSAPG                          GI 2245671

359  ----------------AVEVFQRPPT                              2280326
281  SQYGTMTRQISRHNSTTSSTSSGGYRRTPS                          GI 2245671
```

FIGURE 3B

```
369 LEEL----------------------SPPPP   2280326
311 VTAQFSAQPHVNGGPLYSQNSISIAPPPP     GI 2245671

378 DEELPLPLDL---------------PPP      2280326
341 MPQLTPQIPLTGFVARVQENIADSPTPPPP    GI 2245671

391 PPLDG-----DELGLPPPPG-----          2280326
371 PPPDDIPMFDDSPPPPPPPPVDYEDEEAAV     GI 2245671

407 ------FGPDEPSWVPASYLEKVVTLYPYT    2280326
401 VQYNDPYADGDPAWAPKNYIEKVVAIYDYT    GI 2245671

431 SQKDNELSFSEGTVICVTRRYSDGWCEGVS    2280326
431 KDKDDELSFMEGAIIYVIKKNDDGWYEGVC    GI 2245671

461 SEGTGFFPGNYVEP----SC              2280326
461 NRVTGLFPGNYVESIMHYTD              GI 2245671
```

FIGURE 3C

```
  1 MPVPASWPHPPDPFLLLTLLLG-LTEVAGE    2462908
  1 MPVPASWPHLPSPFLLMTLLLGRLTGVAGE    GI 2052058

30 EELQMIQPEKLLLVTVGKTATLHCTVTSLL    2462908
 31 DELQVIQPEKSVSVAAGESATLRCAMTSLI    GI 2052058

60 PVGPVLWFRGVGPGRELIYNQKEGHFPRVT    2462908
 61 PVGPIMWFRGAGAGRELIYNQKEGHFPRVT    GI 2052058

90 TVSDLTKRNNMDFSIRISSITPADVGTYYC    2462908
 91 TVSELTKRNNLNFSISISNITPADAGTYYC    GI 2052058

120 VKFRKGSPENVEFKSGPGTEMAL-------    2462908
121 VKFRKGSPDDVEFKSGAGTELSVRAKPSAP    GI 2052058

143 -----------------------------    2462908
151 VVSGPAVRATPEHTVSFTCESHGFSPRDIT    GI 2052058

143 -----------------------------    2462908
181 LKWFKNGNELSDFQTNVDPAGDSVSYSIHS    GI 2052058
```

FIGURE 4A

| | | | | |
|---|---|---|---|---|
| 143 | — — — — — — — — — — — — — — — — — — — — — — — — — — — — — — — — — — — — — — — — — — — — — — — — — — — — — — — — — — | — G G P A S | 2462908 |
| 211 | T A R V V L T R G D V H S Q V I C E M A H I T L Q | G D P L R | GI 2052058 |
| 148 | — — — — — — — — S L T A L — — — — — — — — — — — — — — — — — — — — — — — — — — — — — — — — — — — — — — — — — — — — — — | | 2462908 |
| 241 | G T A N L S E A I R V P P T L E V T Q Q P M R A E N Q A N V | | GI 2052058 |
| 153 | — — — — — — — — — — — — — — — — — — — — — — — — — — — — — — | | 2462908 |
| 271 | T C Q V S N F Y P R G L Q L T W L E N G N V S R T E T A S T | | GI 2052058 |
| 153 | — — — — — — — — — — — — — — — — — — — — — — — — — — — — — — | | 2462908 |
| 301 | L I E N K D G T Y N W M S W L L V N T C A H R D D V V L T C | | GI 2052058 |
| 153 | — — — — — — — — — — — — — — — — — — — — — — — — — — — — — — | | 2462908 |
| 331 | Q V E H D G Q Q A V S K S Y A L E I S A H Q K E H G S D I T | | GI 2052058 |
| 153 | — — — — — — — — — — — L I A V L L G P — — — — — — — — — | — I | 2462908 |
| 361 | H E P A L A P T A P L L V A L L L G P K L L L V V G V S A | I | GI 2052058 |
| 163 | Y V P W K Q K T | | 2462908 |
| 391 | Y I C W K Q K A | | GI 2052058 |

FIGURE 4B

CYTOKINE SIGNAL REGULATORS

This application is a divisional application of U.S. application Ser. No. 09/189,035, filed Nov. 10, 1998 now U.S. Pat. No. 6,020,165, issued Feb. 1, 2000.

FIELD OF THE INVENTION

This invention relates to nucleic acid and amino acid sequences of cytokine signal regulators and to the use of these sequences in the diagnosis, treatment, and prevention of cell proliferative and immune disorders.

BACKGROUND OF THE INVENTION

Cytokines are chemicals produced by one cell to affect a response in another cell. Cytokines are secreted proteins, found in the extracellular environment, which interact with specific target cells to communicate information regarding the status of the organism. In this way, cytokines control the survival, growth, and differentiation of cells by eliciting an appropriate biological response in the target tissue. For example, cytokines are produced in response to a microbial infection and trigger increased white blood cell production, function, and chemotaxis. Cytokines may be constitutively produced to maintain a steady state, such as continued cell survival and selection within the nervous system. Examples of cytokines include growth factors, interleukins, and interferons.

Cytokines interact with a target through receptors expressed on the surface of the responsive cell. Cytokines bind with hemopoietin receptors, receptor kinases, and tumor necrosis factor (TNF)/nerve growth factor (NGF) receptors by bringing together two receptor subunits. This dimerization of receptor subunits transmits a signal through the plasma membrane to the cell cytoplasm. In the case of protein kinase receptors, such as the receptors for epidermal growth factor (EGF) and insulin, the juxtaposition of the two receptor subunit cytoplasmic domains activates their intrinsic tyrosine kinase activity. As a result, the subunits phosphorylate each other. The resulting phosphorylated tyrosine residues then interact with cytoplasmic proteins containing src homology 2 (SH2) domains. SH2-containing proteins that interact with phosphorylated receptor molecules include phosphatidylinositol 3'-kinase, src kinase family members, GRB2, and shc. These SH2 containing proteins are often associated with other cytoplasmic proteins, such as members of the small, monomeric GTP-binding protein families Ras and Rho, and phosphatases, such as the phosphotyrosine phosphatase SHP-2. The signaling complexes formed by these interactions can initiate signal cascades, such as the kinase cascade involving raf and mitogen activated protein (MAP) kinase, which result in transcriptional regulation and cytoskeleton reorganization. Hemopoietin and TNF/NGF receptors, though they have no intrinsic kinase activity, still activate many of the same signal cascades within responding cells.

Many of the kinases involved in cytokine signaling cascades were first identified as products of oncogenes in cancer cells in which kinase activation was no longer subject to normal cellular controls. In fact, about one third of the known oncogenes encode protein kinases. Furthermore, cellular transformation (oncogenesis) is often accompanied by increased tyrosine phosphorylation activity (Carbonneau, H. and Tonks, N. K. (1992) Annu. Rev. Cell Biol. 8:463–93). Thus, the cell must have regulatory systems which keep the cytokine signaling cascades under appropriate control.

Eps8 is a protein which associates with and is phosphorylated by the EGF receptor. Human tumor cell lines contain high constitutive levels of tyrosine-phosphorylated Eps8, and overexpression of Eps8 in NIH3T3 cells expressing the EGF receptor (EGFR) leads to an enhanced mitogenic response and cell overgrowth (Provenzano, C. et al. (1998) Exp. Cell Res. 242:186–200). A family of molecules, which include ABI (Abl interactor protein)-1 and ABI-2/e3B1, interact with tyrosine kinases, such as the src-like kinase Abl, and Eps8. Overexpression of ABI-2/e3B1 in NIH3T3 cells expressing EGFR inhibits the mitogenic response and cell growth. Thus, the ABI family of proteins function as negative regulators of cytokine signaling (Ziemnicka-Kotula, D. et al. (1998) J. Biol. Chem. 273:13681–13692).

The SH2-containing phosphotyrosine phosphatases, SHP-1 and SHP-2, are involved in cytokine signaling. SHP-1, the hemopoietic cell phosphatase, is a potent inhibitor of signaling, whereas SHP-2 is a positive signal transducer for several cytokines. A family of transmembrane glycoproteins, called SIRPs (signal regulatory proteins), are substrates of tyrosine kinases. Phosphorylated SIRPs bind to SHP-2 and have a negative effect on cell response induced by cytokines, including an inhibition of growth factor-induced DNA synthesis. This inhibition correlates with reduced MAP kinase activation in SIRP-transfected NIH3T3 cells stimulated with insulin or EGF. SIRP overexpression also suppressed transformation of NIH3T3 cells by a retrovirus carrying the v-fms oncogene (Kharitonenkov, A. et al. (1997) Nature 386:181–186).

The discovery of new cytokine signal regulators and the polynucleotides encoding them satisfies a need in the art by providing new compositions which are useful in the diagnosis, prevention, and treatment of cell proliferative and immune disorders.

SUMMARY OF THE INVENTION

The invention features substantially purified polypeptides, cytokine signal regulators, referred to collectively as "CKSR" and individually as "CKSR-1" and "CKSR-2". In one aspect, the invention provides a substantially purified polypeptide comprising an amino acid sequence selected from the group consisting of SEQ ID NO:1, SEQ ID NO:2, and fragments thereof.

The invention further provides a substantially purified variant having at least 90% amino acid identity to at least one of the amino acid sequences selected from the group consisting of SEQ ID NO:1, SEQ ID NO:2, and fragments thereof. The invention also provides an isolated and purified polynucleotide encoding the polypeptide comprising an amino acid sequence selected from the group consisting of SEQ ID NO:1, SEQ ID NO:2, and fragments thereof. The invention also includes an isolated and purified polynucleotide variant having at least 70% polynucleotide sequence identity to the polynucleotide encoding the polypeptide comprising an amino acid sequence selected from the group consisting of SEQ ID NO:1, SEQ ID NO:2, and fragments thereof.

Additionally, the invention provides an isolated and purified polynucleotide which hybridizes under stringent conditions to the polynucleotide encoding the polypeptide comprising an amino acid sequence selected from the group consisting of SEQ ID NO:1, SEQ ID NO:2, and fragments thereof. The invention also provides an isolated and purified polynucleotide having a sequence which is complementary to the polynucleotide encoding the polypeptide comprising the amino acid sequence selected from the group consisting of SEQ ID NO:1, SEQ ID NO:2, and fragments thereof.

The invention also provides an isolated and purified polynucleotide comprising a polynucleotide sequence selected from the group consisting of SEQ ID NO:3, SEQ ID NO:4, and fragments thereof. The invention further provides an isolated and purified polynucleotide variant having at least 70% polynucleotide sequence identity to the polynucleotide sequence selected from the group consisting of SEQ ID NO:3, SEQ ID NO:4, and fragments thereof. The invention also provides an isolated and purified polynucleotide having a sequence which is complementary to the polynucleotide comprising a polynucleotide sequence selected from the group consisting of SEQ ID NO:3, SEQ ID NO:4, and fragments thereof.

The invention also provides a method for detecting a polynucleotide in a sample containing nucleic acids, the method comprising the steps of (a) hybridizing the complement of the polynucleotide sequence to at least one of the polynucleotides of the sample, thereby forming a hybridization complex; and (b) detecting the hybridization complex, wherein the presence of the hybridization complex correlates with the presence of a polynucleotide in the sample. In one aspect, the method further comprises amplifying the polynucleotide prior to hybridization.

The invention further provides an expression vector containing at least a fragment of the polynucleotide encoding the polypeptide comprising an amino acid sequence selected from the group consisting of SEQ ID NO:1, SEQ ID NO:2, and fragments thereof. In another aspect, the expression vector is contained within a host cell.

The invention also provides a method for producing a polypeptide, the method comprising the steps of: (a) culturing the host cell containing an expression vector containing at least a fragment of a polynucleotide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1, SEQ ID NO:2, and fragments thereof, in conjunction with a suitable pharmaceutical carrier.

The invention further includes a purified antibody which binds to a polypeptide selected from the group consisting of SEQ ID NO:1, SEQ ID NO:2, and fragments thereof. The invention also provides a purified agonist and a purified antagonist to the polypeptide.

The invention also provides a method for treating or preventing a disorder associated with decreased expression or activity of CKSR, the method comprising administering to a subject in need of such treatment an effective amount of a pharmaceutical composition comprising a substantially purified polypeptide having the amino acid sequence selected from the group consisting of SEQ ID NO:1, SEQ ID NO:2, and fragments thereof, in conjunction with a suitable pharmaceutical carrier.

The invention also provides a method for treating or preventing a disorder associated with increased expression or activity of CKSR, the method comprising administering to a subject in need of such treatment an effective amount of an antagonist of a polypeptide having an amino acid sequence selected from the group consisting of SEQ ID NO:1, SEQ ID NO:2, and fragments thereof.

BRIEF DESCRIPTION OF THE FIGURES AND TABLE

FIGS. 1A, 1B, 1C, 1D, 1E, 1F, and 1G show the amino acid sequence (SEQ ID NO:1) and nucleic acid sequence (SEQ ID NO:3) of CKSR-1. The alignment was produced using MACDNASIS PRO software (Hitachi Software Engineering, South San Francisco Calif.).

FIGS. 2A, 2B, and 2C show the amino acid sequence (SEQ ID NO:2) and nucleic acid sequence (SEQ ID NO:4) of CKSR-2. The alignment was produced using MACDNASIS PRO software.

FIGS. 3A, 3B, and 3C show the amino acid sequence alignment between CKSR-1 (2280326; SEQ ID NO:1) and human e3B1 (GI 2245671; SEQ ID NO:5), produced using the multisequence alignment program of LASERGENE software (DNASTAR, Madison Wis.).

FIGS. 4A and 4B show the amino acid sequence alignment between CKSR-2 (2462908; SEQ ID NO:2) and human SIRP-β1 (GI 2052058; SEQ ID NO:6), produced using the multisequence alignment program of LASERGENE software (DNASTAR, Madison Wis.).

Table 1 shows the programs, their descriptions, references, and threshold parameters used to analyze CKSR.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

DEFINITIONS

"CKSR" refers to the amino acid sequences of substantially purified CKSR obtained from any species, particularly a mammalian species, including bovine, ovine, porcine, murine, equine, and preferably the human species, from any source, whether natural, synthetic, semi-synthetic, or recombinant.

The term "agonist" refers to a molecule which, when bound to CKSR, increases or prolongs the duration of the effect of CKSR. Agonists may include proteins, nucleic acids, carbohydrates, or any other molecules which bind to and modulate the effect of CKSR.

An "allelic variant" is an alternative form of the gene encoding CKSR. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding CKSR include those sequences with deletions, insertions, or substitutions of different nucleotides, resulting in a polynucleotide the same as CKSR or a polypeptide with at least one functional characteristic of CKSR. Included within this definition are polymorphisms which may or may not be readily detectable using a particular oligonucleotide probe of the polynucleotide encoding CKSR, and improper or unexpected hybridization to allelic variants, with a locus other than the normal chromosomal locus for the polynucleotide sequence encoding CKSR. The encoded protein may also be "altered," and may contain deletions, insertions, or substitutions of amino acid residues which produce a silent change and result in a functionally equivalent CKSR. Deliberate amino acid substitutions may be made on the basis of similarity in polarity, charge, solubility, hydrophobicity, hydrophilicity, and/or the amphipathic nature of the residues, as long as the biological or immunological activity of CKSR is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence" refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of CKSR which are preferably at least 5 to about 15 amino acids in length, most preferably at least 14 amino acids, and which retain some biological activity or immunological activity of CKSR. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which, when bound to CKSR, decreases the amount or the duration of the effect of the biological or immunological activity of CKSR. Antagonists may include proteins, nucleic acids, carbohydrates, antibodies, or any other molecules which decrease the effect of CKSR.

The term "antibody" refers to intact molecules as well as to fragments thereof, such as Fab, F(ab')$_2$, and Fv fragments, which are capable of binding the epitopic determinant. Antibodies that bind CKSR polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

The term "biologically active," refers to a protein having structural, regulatory, or biochemical functions of a naturally occurring molecule. Likewise, "immunologically active" refers to the capability of the natural, recombinant, or synthetic CKSR, or of any oligopeptide thereof, to induce a specific immune response in appropriate animals or cells and to bind with specific antibodies.

The terms "complementary" or "complementarity" refer to the natural binding of polynucleotides by base pairing. For example, the sequence "5' A—G—T 3'" bonds to the complementary sequence "3' T—C—A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence" refer broadly to any composition containing the given polynucleotide or amino acid sequence. The composition may comprise a dry formulation or an aqueous solution. Compositions comprising polynucleotide sequences encoding CKSR or fragments of CKSR may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" to a nucleic acid sequence which has been resequenced to resolve uncalled bases, extended using XL-PCR kit (Perkin-Elmer, Norwalk Conn.) in the 5' and/or the 3' direction, and resequenced, or which has been assembled from the overlapping sequences of more than one Incyte Clone using a computer program for fragment assembly, such as the GELVIEW fragment Assembly system (GCG, Madison Wis.). Some sequences have been both extended and assembled to produce the consensus sequence.

The term "correlates with expression of a polynucleotide" indicates that the detection of the presence of nucleic acids, the same or related to a nucleic acid sequence encoding CKSR, by northern analysis is indicative of the presence of nucleic acids encoding CKSR in a sample, and thereby correlates with expression of the transcript from the polynucleotide encoding CKSR.

A "deletion" refers to a change in the amino acid or nucleotide sequence that results in the absence of one or more amino acid residues or nucleotides.

The term "derivative" refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity" refers to a degree of complementarity. There may be partial similarity or complete similarity. The word "identity" may substitute for the word "similarity." A partially complementary sequence that at least partially inhibits an identical sequence from hybridizing to a target nucleic acid, is referred to as "substantially similar." The inhibition of hybridization of the completely complementary sequence to the target sequence may be examined using a hybridization assay (Southern or northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Madison Wis.) which creates alignments between two or more sequences according to methods selected by the user, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs) are linear microchromosomes which may contain DNA sequences of about 6 kb to 10 Mb in size, and which contain all of the elements required for stable mitotic chromosome segregation and maintenance.

The term "humanized antibody" refers to antibody molecules in which the amino acid sequence in the non-antigen binding regions has been altered so that the antibody more closely resembles a human antibody, and still retains its original binding ability.

"Hybridization" refers to any process by which a strand of nucleic acid binds with a complementary strand through base pairing.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition" refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray" refers to an arrangement of distinct polynucleotides on a substrate.

The terms "element" or "array element" in a microarray context, refer to hybridizable polynucleotides arranged on the surface of a substrate.

The term "modulate" refers to a change in the activity of CKSR. For example, modulation may cause an increase or a decrease in protein activity, binding characteristics, or any other biological, functional, or immunological properties of CKSR.

The phrases "nucleic acid" or "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked" refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. "Oligonucleotide" is substantially equivalent to the terms "amplimer," "primer," "oligomer," and "probe," as these terms are commonly defined in the art.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

The term "sample" is used in its broadest sense. A sample suspected of containing nucleic acids encoding CKSR, or fragments thereof, or CKSR itself, may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of CKSR polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to CKSR. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

THE INVENTION

The invention is based on the discovery of new human cytokine signal regulators (CKSR), the polynucleotides encoding CKSR, and the use of these compositions for the diagnosis, treatment, or prevention of cell proliferative and immune disorders.

Nucleic acids encoding the CKSR-1 of the present invention were identified in Incyte Clone 2280326 from the prostate cDNA library (PROSNON01) using a computer search for nucleotide and/or amino acid sequence alignments. A consensus sequence, SEQ ID NO:3, was derived from the following overlapping and/or extended nucleic acid sequences: Incyte Clones 3865321H1 (BRAITUT07), 2454448F6 (ENDANOT01), 2280326H1 (PROSNON01), 3677077H1 (PLACNOT07), 825309R1 (PROSNOT06), 1675605F6 (BLADNOT05),3187881 H1 (THYMNON04), 1513011T1 (PANCTUT01), and 2189346T6 (PROSNOT26).

In one embodiment, the invention encompasses a polypeptide comprising the amino acid sequence of SEQ ID NO:1, as shown in FIGS. 1A–G. CKSR is 476 amino acids in length and has one potential N-glycosylation sites at residue N132; one potential cAMP- and cGMP-dependent protein kinase phosphorylation site at residue S452; nine potential casein kinase II phosphorylation sites at residues S51, S58, T95, T124, S349, T368, S418, S431, and S438; and nine potential protein kinase C phosphorylation sites at residues T73, T124, T151, T182, S277, S280, T335, S431, and T448. PFAM, BLOCKS, and PRINTS identify a potential Src homology 3 (SH3) domain from residue E421 through S475. As shown in FIGS. 3A, 3B, and 3C, CKSR-1 has chemical and structural similarity with human e3B1 (GI 2245671; SEQ ID NO:5). In particular, CKSR-1 and e3B1 share 32% identity. A fragment of SEQ ID NO:3 from about nucleotide 447 to about nucleotide 509 is useful in hybridization or amplification technologies to identify SEQ ID NO:3 and to distinguish between SEQ ID NO:3 and a related sequence.

Northern analysis shows the expression of CKSR-1 in various libraries, at least 50% of which are associated with cancer and at least 38% of which are associated with the immune response. Of particular note is the expression of CKSR-1 in cardiovascular, gastrointestinal, reproductive, and hematopoietic/immune tissues.

Nucleic acids encoding the CKSR-2 of the present invention were identified in Incyte Clone 2462908 from the thyroid tissue cDNA library (THYRNOT08) using a computer search for nucleotide and/or amino acid sequence alignments. A consensus sequence, SEQ ID NO:4, was derived from the following overlapping and/or extended nucleic acid sequences: Incyte Clones 2462908X302D1 and 2462908H1 (THYRNOT08), and 173576x301B2 (COLNNOT22).

In one embodiment, the invention encompasses a polypeptide comprising the amino acid sequence of SEQ ID NO:2, as shown in FIGS. 2A, 2B, and 2C. CKSR-2 is 170 amino acids in length and has one potential cAMP- and cGMP-dependent protein kinase phosphorylation sites at residues S126; two potential casein kinase II phosphorylation sites at residues T90 and T110; and two potential protein kinase C phosphorylation sites at residues T95 and S103. SPScan and HMM-based analysis identify a potential signal peptide from residue M1 through G28, and PFAM identifies a potential immunoglobulin signature from residue G46 through K121. As shown in FIGS. 4A and 4B, CKSR-2 has chemical and structural similarity with human SIRP-β1 (GI 2052058; SEQ ID NO:6). In particular, CKSR-2 and SIRP-β1 share 69% identity. A fragment of SEQ ID NO:4 from about nucleotide 438 to about nucleotide 482 is useful in hybridization or amplification technologies to identify SEQ ID NO:4 and to distinguish between SEQ ID NO:4 and a related sequence.

Northern analysis shows the expression of CKSR-2 in various libraries, at least 67% of which are associated with cancer and at least 33% of which are associated with the immune response. Of particular note is the expression of CKSR-2 in cardiovascular, gastrointestinal, and endocrine tissues.

The invention also encompasses CKSR variants. A preferred CKSR variant is one which has at least about 80%, more preferably at least about 90%, and most preferably at least about 95% amino acid sequence identity to the CKSR amino acid sequence, and which contains at least one functional or structural characteristic of CKSR.

The invention also encompasses polynucleotides which encode CKSR. In a particular embodiment, the invention encompasses a polynucleotide sequence comprising a sequence selected from the group consisting of SEQ ID NO:3 and SEQ ID NO:4, which encodes CKSR.

The invention also encompasses a variant of a polynucleotide sequence encoding CKSR. In particular, such a variant polynucleotide sequence will have at least about 70%, more preferably at least about 85%, and most preferably at least about 95% polynucleotide sequence identity to the polynucleotide sequence encoding CKSR. A particular aspect of the invention encompasses a variant of a polynucleotide sequence comprising a sequence selected from the group consisting of SEQ ID NO:3 and SEQ ID NO:4 which has at least about 70%, more preferably at least about 85%, and most preferably at least about 95% polynucleotide sequence identity to a nucleic acid sequence selected from the group consisting of SEQ ID NO:3 and SEQ ID NO:4. Any one of the polynucleotide variants described above can encode an amino acid sequence which contains at least one functional or structural characteristic of CKSR.

It will be appreciated by those skilled in the art that as a result of the degeneracy of the genetic code, a multitude of polynucleotide sequences encoding CKSR, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring CKSR, and all such variations are to be considered as being specifically disclosed.

Although nucleotide sequences which encode CKSR and its variants are preferably capable of hybridizing to the nucleotide sequence of the naturally occurring CKSR under appropriately selected conditions of stringency, it may be advantageous to produce nucleotide sequences encoding CKSR or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding CKSR and its derivatives without altering the encoded amino acid sequences include the production of RNA transcripts having more desirable properties, such as a greater half-life, than transcripts produced from the naturally occurring sequence.

The invention also encompasses production of DNA sequences which encode CKSR and CKSR derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding CKSR or any fragment thereof.

Also encompassed by the invention are polynucleotide sequences that are capable of hybridizing to the claimed polynucleotide sequences, and, in particular, to those shown in SEQ ID NO:3, SEQ ID NO:4 and fragments thereof under various conditions of stringency. (See, e.g., Wahl, G. M. and S. L. Berger (1987) Methods Enzymol. 152:399–407; Kimmel, A. R. (1987) Methods Enzymol. 152:507–511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 $\mu$g/Ml denatured salmon sperm DNA (ssDNA). In a most preferred embodiment, hybridization will occur at 42° C. in 250 mM NaCl, 25 mM trisodium citrate, 1% SDS, 50% formamide, and 200 $\mu$g/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0. 1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Perkin-Elmer), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 (Hamilton, Reno Nev.), Peltier thermal cycler 200 (PTC200; MJ Research, Watertown Mass.) and the ABI CATALYST 800 (Perkin-Elmer). Sequencing is then carried out using either ABI 373 or 377 DNA sequencing systems (Perkin-Elmer) or the MEGABACE 1000 DNA sequencing system (Molecular Dynamics, Sunnyvale Calif.). The resulting sequences are analyzed using a variety of algorithms which are well known in the art. (See, e.g., Ausubel, F. M. (1997) *Short Protocols in Molecular Biology*, John Wiley & Sons, New York N.Y., unit 7.7; Meyers, R. A. (1995) *Molecular Biolog and Biotechnology*, Wiley VCH, New York N.Y., pp. 856–853.)

The nucleic acid sequences encoding CKSR may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 primer analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Perkin-Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode CKSR may be cloned in recombinant DNA molecules that direct expression of CKSR, or fragments or functional equivalents thereof, in appropriate host cells. Due to the inherent degeneracy of the genetic code, other DNA sequences which encode substantially the same or a functionally equivalent amino acid sequence may be produced and used to express CKSR.

The nucleotide sequences of the present invention can be engineered using methods generally known in the art in order to alter CKSR-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding CKSR may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, CKSR itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431A peptide synthesizer (Perkin-Elmer). Additionally, the amino acid sequence of CKSR, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) Proteins, Structures and Molecular Properties, WH Freeman, New York N.Y.)

In order to express a biologically active CKSR, the nucleotide sequences encoding CKSR or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding CKSR. Such elements may vary in their strength and specificity. Specific initiation signals may also be used to achieve more efficient translation of sequences encoding CKSR. Such signals include the ATG initiation codon and adjacent sequences, e.g. the Kozak sequence. In cases where sequences encoding CKSR and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding CKSR and appropriate transcriptional and translational control elements. These methods include in vitro recombinant DNA techniques, synthetic techniques, and in vivo genetic recombination. (See, e.g., Sambrook, J. et al. (1989) Molecular Cloning, A Laboratory Manual, Cold Spring Harbor Press, Plainview N.Y., ch. 4, 8, and 16–17; Ausubel, F. M. et al. (1995) Current Protocols in Molecular Biology, John Wiley & Sons, New York N.Y., ch. 9, 13, and 16.)

A variety of expression vector/host systems may be utilized to contain and express sequences encoding CKSR. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding CKSR. For example, routine cloning, subcloning, and propagation of polynucleotide sequences encoding CKSR can be achieved using a multifunctional E. coli vector such as PBLUESCRIPT (Stratagene, La Jolla Calif.) or PSPORT1 plasmid (Life Technologies). Ligation of sequences encoding CKSR into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of CKSR are needed, e.g. for the production of antibodies, vectors which direct high level expression of CKSR may be used. For example, vectors containing the strong, inducible T5 or T7 bacteriophage promoter may be used.

Yeast expression systems may be used for production of CKSR. A number of vectors containing constitutive or inducible promoters, such as alpha factor, alcohol oxidase, and PGH, may be used in the yeast Saccharomvces cerevisiae or Pichia pastoris. In addition, such vectors direct either the secretion or intracellular retention of expressed proteins and enable integration of foreign sequences into the host genome for stable propagation. (See, e.g., Ausubel, 1995, supra; Grant et al. (1987) Methods Enzymol. 153:516–54; and Scorer, C. A. et al. (1994) Bio/Technology 12:181–184.)

Plant systems may also be used for expression of CKSR. Transcription of sequences encoding CKSR may be driven viral promoters, e.g., the 35S and 19S promoters of CaMV used alone or in combination with the omega leader sequence from TMV (Takamatsu, N. (1987) EMBO J. 6:307–311). Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., The McGraw Hill Yearbook of Science and Technology (1992) McGraw Hill, New York N.Y., pp. 191–196.)

In mammalian cells, a number of viral-based expression systems may be utilized. In cases where an adenovirus is used as an expression vector, sequences encoding CKSR may be ligated into an adenovirus transcription/translation complex consisting of the late promoter and tripartite leader sequence. Insertion in a non-essential E1 or E3 region of the viral genome may be used to obtain infective virus which expresses CKSR in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat Genet. 15:345–355.)

For long term production of recombinant proteins in mammalian systems, stable expression of CKSR in cell lines is preferred. For example, sequences encoding CKSR can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk$^-$ or apr$^-$ cells, respectively. (See, e.g., Wigler, M. et al. (1977) Cell 11:223–232; Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides, neomycin and G-418; and als and pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al. (1981) J. Mol. Biol. 150:1–14.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121–13 1.)

Although the presence/absence of marker gene expression suggests that the gene of interest is also present, the presence and expression of the gene may need to be confirmed. For example, if the sequence encoding CKSR is inserted within a marker gene sequence, transformed cells containing sequences encoding CKSR can be identified by the absence of marker gene function. Alternatively, a marker gene can be placed in tandem with a sequence encoding CKSR under the control of a single promoter. Expression of the marker gene in response to induction or selection usually indicates expression of the tandem gene as well.

In general, host cells that contain the nucleic acid sequence encoding CKSR and that express CKSR may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of CKSR using either specific polyclonal or monoclonal antibodies are known in the art. Examples of such techniques include enzyme-linked immunosorbent assays (ELISAs), radio immunoassays (RIAs), and fluorescence activated cell sorting (FACS). A two-site, monoclonal-based immunoassay utilizing monoclonal antibodies reactive to two non-interfering epitopes on CKSR is preferred, but a competitive binding assay may be employed. These and other assays are well known in the art. (See, e.g., Hampton, R. et al. (1990) *Serological Methods, a Laboratory Manual*, APS Press, St Paul Minn., Sect. IV; Coligan, J. E. et al. (1997) *Current Protocols in Immunology*, Greene Pub. Associates and Wiley-Interscience, New York N.Y.; and Pound, J. D. (1998) *Immunochemical Protocols*, Humana Press, Totowa N.J.).

A wide variety of labels and conjugation techniques are known by those skilled in the art and may be used in various nucleic acid and amino acid assays. Means for producing labeled hybridization or PCR probes for detecting sequences related to polynucleotides encoding CKSR include oligolabeling, nick translation, end-labeling, or PCR amplification using a labeled nucleotide. Alternatively, the sequences encoding CKSR, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding CKSR may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode CKSR may be designed to contain signal sequences which direct secretion of CKSR through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38), are available from the American Type Culture Collection (ATCC, Bethesda Md.) and may be chosen to ensure the correct modification and processing of the foreign protein.

In another embodiment of the invention, natural, modified, or recombinant nucleic acid sequences encoding CKSR may be ligated to a heterologous sequence resulting in translation of a fusion protein in any of the aforementioned host systems. For example, a chimeric CKSR protein containing a heterologous moiety that can be recognized by a commercially available antibody may facilitate the screening of peptide libraries for inhibitors of CKSR activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the CKSR encoding sequence and the heterologous protein sequence, so that CKSR may be cleaved away from the heterologous moiety following purification. Methods for fusion protein expression and purification are discussed in Ausubel (1995, supra, ch 10). A variety of commercially available kits may also be used to facilitate expression and purification of fusion proteins.

In a further embodiment of the invention, synthesis of radiolabeled CKSR may be achieved in vitro using the TNT rabbit reticulocyte lysate or wheat germ extract systems (Promega). These systems couple transcription and translation of protein-coding sequences operably associated with the T7, T3, or SP6 promoters. Translation takes place in the presence of a radiolabeled amino acid precursor, preferably $^{35}$S-methionine.

Fragments of CKSR may be produced not only by recombinant production, but also by direct peptide synthesis using solid-phase techniques. (See, e.g., Creighton, supra, pp. 55–60.) Protein synthesis may be performed by manual techniques or by automation. Automated synthesis may be achieved, for example, using the ABI 431A peptide synthesizer (Perkin-Elmer). Various fragments of CKSR may be synthesized separately and then combined to produce the full length molecule.

THERAPEUTICS

Chemical and structural similarity, e.g., in the context of sequences and motifs, exists between regions of CKSR and cytokine signaling proteins. In addition, the expression of CKSR is closely associated with cardiovascular and gastrointestinal tissues, cancer, and the immune response. Therefore, CKSR appears to play a role in cell proliferative and immune disorders. In the treatment of disorders associated with increased CKSR expression or activity, it is desirable to decrease the expression or activity of CKSR. In the treatment of the above conditions associated with decreased CKSR expression or activity, it is desirable to increase the expression or activity of CKSR.

Therefore, in one embodiment, CKSR or a fragment or derivative thereof may be administered to a subject to treat or prevent a disorder associated with decreased expression or activity of CKSR. Examples of such disorders include, but are not limited to, a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and an immune disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyenodocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

In another embodiment, a vector capable of expressing CKSR or a fragment or derivative thereof may be administered to a subject to treat or prevent a disorder associated with decreased expression or activity of CKSR including, but not limited to, those described above.

In a further embodiment, a pharmaceutical composition comprising a substantially purified CKSR in conjunction with a suitable pharmaceutical carrier may be administered to a subject to treat or prevent a disorder associated with decreased expression or activity of CKSR including, but not limited to, those provided above.

In still another embodiment, an agonist which modulates the activity of CKSR may be administered to a subject to treat or prevent a disorder associated with decreased expression or activity of CKSR including, but not limited to, those listed above.

In a further embodiment, an antagonist of CKSR may be administered to a subject to treat or prevent a disorder associated with increased expression or activity of CKSR. Examples of such disorders include, but are not limited to, those described above. In one aspect, an antibody which specifically binds CKSR may be used directly as an antagonist or indirectly as a targeting or delivery mechanism for bringing a pharmaceutical agent to cells or tissue which express CKSR.

In an additional embodiment, a vector expressing the complement of the polynucleotide encoding CKSR may be administered to a subject to treat or prevent a disorder associated with increased expression or activity of CKSR including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of CKSR may be produced using methods which are generally known in the art. In particular, purified CKSR may be used to produce antibodies or to screen libraries of pharmaceutical agents to identify those which specifically bind CKSR. Antibodies to CKSR may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with CKSR or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to CKSR have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of CKSR amino acids may be fused with those of another protein, such as KLH, and antibodies to the chimeric molecule may be produced.

Monoclonal antibodies to CKSR may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855;Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce CKSR-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; Winter, G. et al. (1991) Nature 349:293–299.)

Antibody fragments which contain specific binding sites for CKSR may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between CKSR and its specific antibody. A two-site, monoclonal-based immunoassay utilizing monoclonal antibodies reactive to two non-interfering CKSR epitopes is preferred, but a competitive binding assay may also be employed (Pound, supra).

Various methods such as Scatchard analysis in conjunction with radioimmunoassay techniques may be used to assess the affinity of antibodies for CKSR. Affinity is expressed as an association constant, $K_a$, which is defined as the molar concentration of CKSR-antibody complex divided by the molar concentrations of free antigen and free antibody under equilibrium conditions. The $K_a$ determined for a preparation of polyclonal antibodies, which are heterogeneous in their affinities for multiple CKSR epitopes, represents the average affinity, or avidity, of the antibodies for CKSR. The $K_a$ determined for a preparation of monoclonal antibodies, which are monospecific for a particular CKSR epitope, represents a true measure of affinity. High-affinity antibody preparations with K ranging from about $10^9$ to $10^{12}$ L/mole are preferred for use in immunoassays in which the CKSR-antibody complex must withstand rigorous manipulations. Low-affinity antibody preparations with $K_a$ ranging from about $10^6$ to $10^7$ L/mole are preferred for use in immunopurification and similar procedures which ultimately require dissociation of CKSR, preferably in active form, from the antibody (Catty, D. (1988) *Antibodies, Volume I: A Practical Approach*, IRL Press, Washington, D.C.; Liddell, J. E. and Cryer, A. (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is preferred for use in procedures requiring precipitation of CKSR-antibody complexes. Procedures for evaluating antibody specificity, titer, and avidity, and guidelines for antibody quality and usage in various applications, are generally available. (See, e.g., Catty, , and Coligan et al. supra.)

In another embodiment of the invention, the polynucleotides encoding CKSR, or any fragment or complement thereof, may be used for therapeutic purposes. In one aspect, the complement of the polynucleotide encoding CKSR may be used in situations in which it would be desirable to block the transcription of the mRNA. In particular, cells may be transformed with sequences complementary to polynucleotides encoding CKSR. Thus, complementary molecules or fragments may be used to modulate CKSR activity, or to achieve regulation of gene function. Such technology is now well known in the art, and sense or antisense oligonucleotides or larger fragments can be designed from various locations along the coding or control regions of sequences encoding CKSR.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding CKSR. (See, e.g., Sambrook, supra; Ausubel, 1995, supra.)

Genes encoding CKSR can be turned off by transforming a cell or tissue with expression vectors which express high levels of a polynucleotide, or fragment thereof, encoding CKSR. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding CKSR. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding CKSR.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding CKSR. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of CKSR, antibodies to CKSR, and mimetics, agonists, antagonists, or inhibitors of CKSR. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdernal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of CKSR, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example CKSR or fragments thereof, antibodies of CKSR, and agonists, antagonists or inhibitors of CKSR, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind CKSR may be used for the diagnosis of disorders characterized by expression of CKSR, or in assays to monitor patients being treated with CKSR or agonists, antagonists, or inhibitors of CKSR. Antibodies useful for diagnostic purposes may be prepared in the same manner as described above for therapeutics. Diagnostic assays for CKSR include methods which utilize the antibody and a label to detect CKSR in human body fluids or in extracts of cells or tissues. The antibodies may be used with or without modification, and may be labeled by covalent or noncovalent attachment of a reporter molecule. A wide variety of reporter molecules, several of which are described above, are known in the art and may be used.

A variety of protocols for measuring CKSR, including ELISAs, RIAs, and FACS, are known in the art and provide a basis for diagnosing altered or abnormal levels of CKSR expression. Normal or standard values for CKSR expression are established by combining body fluids or cell extracts taken from normal mammalian subjects, preferably human, with antibody to CKSR under conditions suitable for complex formation. The amount of standard complex formation may be quantitated by various methods, preferably by photometric means. Quantities of CKSR expressed in subject samples from biopsied tissues are compared with the standard values. Deviation between standard and subject values establishes the parameters for diagnosing disease.

In another embodiment of the invention, the polynucleotides encoding CKSR may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of CKSR may be correlated with disease. The diagnostic assay may be used to determine absence, presence, and excess expression of CKSR, and to monitor regulation of CKSR levels during therapeutic intervention.

In one aspect, hybridization with PCR probes which are capable of detecting polynucleotide sequences, including genomic sequences, encoding CKSR or closely related molecules may be used to identify nucleic acid sequences which encode CKSR. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding CKSR, allelic variants, or related sequences.

Probes may also be used for the detection of related sequences, and should preferably have at least 50% sequence identity to any of the CKSR encoding sequences. The hybridization probes of the subject invention may be DNA or RNA and may be derived from the sequence of SEQ ID NO:3 and SEQ ID NO:4 or from genomic sequences including promoters, enhancers, and introns of the CKSR gene.

Means for producing specific hybridization probes for DNAs encoding CKSR include the cloning of polynucleotide sequences encoding CKSR or CKSR derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$P or $^{35}$S, or by enzymatic labels, such as alkaline phosphatase coupled to the probe via avidin/biotin coupling systems, and the like.

Polynucleotide sequences encoding CKSR may be used for the diagnosis of disorders associated with expression of CKSR. Examples of such disorders include, but are not limited to, a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and an immune disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyenodocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma. The polynucleotide sequences encoding CKSR may be used in Southern or northern analysis, dot blot, or other membrane-based technologies; in PCR technologies; in dipstick, pin, and multiformat ELISA-like assays; and in microarrays utilizing fluids or tissues from patients to detect altered CKSR expression. Such qualitative or quantitative methods are well known in the art.

In a particular aspect, the nucleotide sequences encoding CKSR may be useful in assays that detect the presence of associated disorders, particularly those mentioned above. The nucleotide sequences encoding CKSR may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding CKSR in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of CKSR, a normal or standard profile for expression is established. This may be accomplished by combining body fluids or cell extracts taken from normal subjects, either animal or human, with a sequence, or a fragment thereof, encoding CKSR, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding CKSR may involve the use of PCR. These oligomers may be chemically synthesized, generated enzymatically, or produced in vitro. Oligomers will preferably contain a fragment of a polynucleotide encoding CKSR, or a fragment of a polynucleotide complementary to the polynucleotide encoding CKSR, and will be employed under optimized conditions for identification of a specific gene or condition. Oligomers may also be employed under less stringent conditions for detection or quantitation of closely related DNA or RNA sequences.

Methods which may also be used to quantitate the expression of CKSR include radiolabeling or biotinylating nucleotides, coamplification of a control nucleic acid, and interpolating results from standard curves. (See, e.g., Melby, P. C. et al. (1993) J. Immunol. Methods 159:235–244; Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662)

In another embodiment of the invention, nucleic acid sequences encoding CKSR may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat Genet. 15:345–355; Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, supra, pp. 965–968.) Examples of genetic map data can be found in various scientific journals or at the Online Mendelian Inheritance in Man (OMIM) site. Correlation between the location of the gene encoding CKSR on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, CKSR, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between CKSR and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with CKSR, or fragments thereof, and washed. Bound CKSR is then detected by methods well known in the art. Purified CKSR can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding CKSR specifically compete with a test compound for binding CKSR. In this manner, antibodies can be used to detect the presence of any peptide which shares one or more antigenic determinants with CKSR.

In additional embodiments, the nucleotide sequences which encode CKSR may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. Construction of cDNA Libraries

PROSNON01

The PROSNON01 normalized cDNA library was constructed from prostate tissue obtained from a 28-year-old Caucasian male.

The frozen tissue was homogenized and lysed in guanidinium isothiocyanate solution using a Polytron PT-3000 homogonizer (Brinkmann Instruments, Westbury, N.Y.). The lysate was centrifuged over a 5.7 M CsCl cushion using a SW28 rotor in a L8-70M ultracentrifuge (Beckman Instruments) for 18 hours at 25,000 rpm at ambient temperature. The RNA was extracted with acid phenol, precipitated using sodium acetate and ethanol, resuspended in RNAse-free water, and treated with DNase. The RNA was extracted with acid phenol and precipitated as before. Poly(A+) RNA was isolated using the OLIGOTEX kit (QIAGEN, Inc., Chatsworth, Calif.).

Poly(A+) RNA was used for cDNA synthesis and library construction according to the recommended protocols in the SUPERSCRIPT plasmid system (Life Technologies). cDNAs were fractionated on a SEPHAROSE CL4B column (Pharmacia Amersham Biotech, Piscataway, N.J.) and those cDNAs exceeding 400 bp were ligated into PSPORT1 (Life Technologies) and subsequently transformed into DH12S competent cells (Life Technologies).

$4.4 \times 10^6$ independent plasmid clones in DH12S cells (Life Technologies) were grown in liquid culture containing 25 mg/L carbenicillin and 1 mg/ml methicillin until the OD600 reached a value of 0.2. The culture was then superinfected with helper phage M13K07 at a 5-fold excess, according to the method of Vieira et al. (1987, *Methods Enzymol.* 153:3–11).

To reduce the number of excess cDNA copies according to their abundance levels in the library, the cDNA library was then normalized in a single round according to the procedure of Soares et al. (1994 *Proc. Natl. Acad. Sci.* 91:9928–9932), with the following modifications. 1) The primer to template ratio in the primer extension reaction was increased from 2:1 to 10:1; 2) the ddNTP concentration was reduced to 1 50 $\mu$M each ddNTP; 3) the reannealing hybridization was extended from 13 to 19 hours; and 4) the single stranded DNA circles of the normalized library were purified by hydroxyapatite chromatography and converted to partially double-stranded by random priming, followed by electroporation into DH10B competent cells (Life Technologies).

THYRNOT08

The THYRNOT08 cDNA library was constructed using RNA isolated from thyroid gland tissue obtained from a 13 year-old Caucasian female during a complete thyroidectomy. Pathology indicated lymphocytic thyroiditis. Patient history included attention deficit disorder. Family history included chronic obstructive asthma, attention deficit disorder, and depressive disorder.

The frozen tissue was homogenized and lysed in TRIZOL reagent (Life Technologies), a monophasic solution of phenol and guanidine isothiocyanate, using a Polytron PT-3000 homogenizer (Brinkmann Instruments, Westbury, N.Y.). After a brief incubation on ice, chloroform was added (1:5 v/v), and the lysate was centrifuged. The upper chloroform layer was removed and the RNA extracted with isopropanol, resuspended in water, and treated with DNase for 25 min at 37° C. Extraction and precipitation were repeated. Poly(A+) RNA was isolated using the OLIGOTEX kit (QIAGEN, Inc., Chatsworth, Calif.).

Poly(A+) RNA was used for cDNA synthesis and library construction according to the recommended protocols in the SUPERSCRIPT plasmid system (Life Technologies). cDNAs were fractionated on a SEPHAROSE CL4B column (Pharmacia Amersham Biotech, Piscataway, N.J.) and those cDNAs exceeding 400 bp were ligated into pINCY (Incyte Pharmaceuticals, Inc., Palo Alto, Calif.) and subsequently transformed into DH5$\alpha$ competent cells (Life Technologies).

II. Isolation of CDNA Clones

Plasmid DNA was released from the cells and purified using the R.E.A.L. Prep 96 plasmid kit (QIAGEN, Inc.). The recommended protocol was employed except for the following changes: 1) the bacteria were cultured in 1 ml of sterile Terrific Broth (Life Technologies) with carbenicillin at 25 mg/L and glycerol at 0.4%; 2) after the cultures were incubated for 19 hours, the cells were lysed with 0.3 ml of lysis buffer; and 3) following isopropanol precipitation, the plasmid DNA pellets were resuspended in 0.1 ml of distilled water. The DNA samples were stored at 4° C.

III. Sequencing and Analysis

The cDNAs were prepared for sequencing using the ABI CATALYST 800 (Perkin-Elmer) or the HYDRA microdispenser (Robbins Scientific) or MICROLAB 2200 (Hamilton) systems in combination with the PTC-200 thermal cyclers (MJ Research). The cDNAs were sequenced using the ABI PRISM 373 or 377 sequencing systems (Perkin-Elmer) and standard ABI protocols, base calling software, and kits. In one alternative, cDNAs were sequenced using the MEGABACE 1000 DNA sequencing system (Molecular Dynamics). In another alternative, the cDNAs were amplified and sequenced using the ABI PRISM BIGDYE Terminator cycle sequencing ready reaction kit (Perkin-Elmer). In yet another alternative, cDNAs were sequenced using solutions and dyes from Amersham Pharmacia Biotech. Reading frames for the ESTs were determined using standard methods (reviewed in Ausubel, 1997, unit 7.7). Some of the cDNA sequences were selected for extension using the techniques disclosed in Example V.

The polynucleotide sequences derived from cDNA, extension, and shotgun sequencing were assembled and analyzed using a combination of software programs which utilize algorithms well known to those skilled in the art. Table 1 summarizes the software programs, descriptions, references, and threshold parameters used. The first column of Table I shows the tools, programs, and algorithms used, the second column provides a brief description thereof, the third column presents the references which are incorporated by reference herein, and the fourth column presents, where applicable, the scores, probability values, and other parameters used to evaluate the strength of a match between two sequences (the higher the probability the greater the homology). Sequences were analyzed using MACDNASIS PRO software (Hitachi Software Engineering, South San Francisco Calif.) and LASERGENE software (DNASTAR).

The polynucleotide sequences were validated by removing vector, linker, and polyA sequences and by masking ambiguous bases, using algorithms and programs based on BLAST, dynamic programing, and dinucleotide nearest neighbor analysis. The sequences were then queried against a selection of public databases such as GenBank primate, rodent, mammalian, vertebrate, and eukaryote databases, and BLOCKS to acquire annotation, using programs based on BLAST, FASTA, and BLIMPS. The sequences were assembled into full length polynucleotide sequences using programs based on Phred, Phrap, and Consed, and were screened for open reading frames using programs based on GeneMark, BLAST, and FASTA. The full length polynucleotide sequences were translated to derive the corresponding full length amino acid sequences, and these full length sequences were subsequently analyzed by querying against databases such as the GenBank databases (described above), SWISS-PROT BLOCKS, PRINTS, Prosite, and Hidden Markov Model (HMM)-based protein family databases such as PFAM. HMM is a probalistic approach which analyzes consensus primary structures of gene families. (See, e.g., Eddy, S. R. (1996) Cur. Opin. Str. Biol. 6:361–365.)

The programs described above for the assembly and analysis of full length polynucleotide and amino acid sequences were also used to identify polynucleotide sequence fragments from SEQ ID NO:3 and SEQ ID NO:4. Fragments from about 20 to about 4000 nucleotides which are useful in hybridization and amplification technologies were described in The Invention section above.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel, 1995, supra, ch. 4 and 16.)

Analogous computer techniques applying BLAST were used to search for identical or related molecules in nucleotide databases such as GenBank or LIFESEQ database (Incyte Pharmaceuticals). This analysis is much faster than multiple membrane-based hybridizations. In addition, the sensitivity of the computer search can be modified to determine whether any particular match is categorized as exact or similar. The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of northern analyses are reported as a percentage distribution of libraries in which the transcript encoding CKSR occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease/condition categories included cancer, inflammation/trauma, cell proliferation, neurological, and pooled. For each category, the number of libraries expressing the sequence of interest was counted and divided by the total number of libraries across all categories. Percentage values of tissue-specific and disease- or condition-specific expression are reported in the description of the invention.

V. Extension of CKSR Encoding Polynucleotides

The full length nucleic acid sequences of SEQ ID NO:3 and SEQ ID NO:4 were produced by extension of an appropriate fragment of the full length molecule using oligonucleotide primers designed from this fragment. One primer was synthesized to initiate 5' extension of the known fragment, and the other primer, to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 μl PICOGREEN quantitation reagent (0.25% (v/v) PICOGREEN; Molecular Probes, Eugene Oreg.) dissolved in 1X TE and 0.5 μl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 μl to 10 μl aliquot of the reaction mixture was analyzed by electrophoresis on a 1% agarose mini-gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were relegated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent E. coli cells. Transformed cells were selected on antibiotic-containing media, individual colonies were picked and cultured overnight at 37° C. in 384-well plates in LB/2x carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethysulphoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Perkin-Elmer).

In like manner, the nucleotide sequences of SEQ ID NO:3 and SEQ ID NO:4 are used to obtain 5' regulatory sequences using the procedure above, oligonucleotides designed for such extension, and an appropriate genomic library.

VI. Labeling and Use of Individual Hybridization Probes

Hybridization probes derived from SEQ ID NO:3 and SEQ ID NO:4 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 $\mu$Ci of [$\gamma$-$^{32}$P] adenosine triphosphate (Amersham Pharmacia Biotech), and T4 polynucleotide kinase (DuPont NEN, Boston Mass.). The labeled. oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba I, or Pvu II (DuPont NEN).

The DNA from each digest is fractionated on a 0.7% agarose gel and transferred to nylon membranes (NYTRAN PLUS, Schleicher & Schuell, Durham N.H.). Hybridization is carried out for 16 hours at 40° C. To remove nonspecific signals, blots are sequentially washed at room temperature under increasingly stringent conditions up to 0.1x saline sodium citrate and 0.5% sodium dodecyl sulfate. After XOMAT-AR film (Eastman Kodak, Rochester N.Y.) is exposed to the blots, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the CKSR-encoding sequences, or any parts thereof, are used to detect, decrease, or inhibit expression of naturally occurring CKSR. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of CKSR. To inhibit transcription, a complementary oligonucleotide is designed from the most unique 5' sequence and used to prevent promoter binding to the coding sequence. To inhibit translation, a complementary oligonucleotide is designed to prevent ribosomal binding to the CKSR-encoding transcript.

IX. Expression of CKSR

Expression and purification of CKSR is achieved using bacterial or virus-based expression systems. For expression of CKSR in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21 (DE3). Antibiotic resistant bacteria express CKSR upon induction with isopropyl beta-D-thiogalactopyranoside (IPTG). Expression of CKSR in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding CKSR by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, CKSR is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from CKSR at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch 10 and 16). Purified CKSR obtained by these methods can be used directly in the following activity assay.

X. Demonstration of CKSR Activity

CKSR activity may be measured by the induction of growth arrest when CKSR is expressed at physiologically elevated levels in transformed mammalian cell lines. CKSR cDNA is subcloned into a mammalian expression vector containing a strong promoter that drives high levels of cDNA expression, and these constructs are stably transfected into a transformed cell line, such as NIH 3T6 or C6, using methods known in the art. An additional plasmid, containing sequences which encode a selectable marker, such as hygromycin resistance, are co-transfected. Expression of a marker protein provides a means to distinguish transfected cells from nontransfected cells and is a reliable predictor of cDNA expression from the recombinant vector. Cells expressing CKSR are compared with control cells, either non-transfected or transfected with vector alone, for characteristics associated with growth arrest. Such characteristics can include, but are not limited to, a reduction in [$^3$H]-thymidine incorporation into newly synthesized DNA, lower doubling and generation times, and decreased culture saturation density. The amount of growth arrest measured is proportional to the activity of CKSR.

XI. Functional Assays

CKSR function is assessed by expressing the sequences encoding CKSR at physiologically elevated levels in mammalian cell culture systems. cDNA is subcloned into a mammalian expression vector containing a strong promoter that drives high levels of cDNA expression. Vectors of choice include pCMV SPORT (Life Technologies) and pCR3.1 (Invitrogen, Carlsbad Calif.), both of which contain the cytomegalovirus promoter. 5–10 µg of recombinant vector are transiently transfected into a human cell line, preferably of endothelial or hematopoietic origin, using either liposome formulations or electroporation. 1–2 µg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York N.Y.

The influence of CKSR on gene expression can be assessed using highly purified populations of cells transfected with sequences encoding CKSR and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding CKSR and other genes of interest can be analyzed by northern analysis or microarray techniques.

XII. Production of CKSR Specific Antibodies

CKSR substantially purified using polyacrylamide gel electrophoresis (PAGE; see, e.g., Harrington, M. G. (1990) Methods Enzymol. 182:488–495), or other purification techniques, is used to immunize rabbits and to produce antibodies using standard protocols.

Alternatively, the CKSR amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides 15 residues in length are synthesized using an ABI 431A Peptide synthesizer (Perkin-Elmer) using fmoc-chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring CKSR Using Specific Antibodies

Naturally occurring or recombinant CKSR is substantially purified by immunoaffinity chromatography using antibodies specific for CKSR. An immunoaffinity column is constructed by covalently coupling anti-CKSR antibody to an activated chromatographic resin, such as CNBr-activated SEPHAROSE (Amersham Pharmacia Biotech). After the coupling, the resin is blocked and washed according to the manufacturer's instructions.

Media containing CKSR are passed over the immunoaffinity column, and the column is washed under conditions that allow the preferential absorbance of CKSR (e.g., high ionic strength buffers in the presence of detergent). The column is eluted under conditions that disrupt antibody/CKSR binding (e.g., a buffer of pH 2 to pH 3, or a high concentration of a chaotrope, such as urea or thiocyanate ion), and CKSR is collected.

XIV. Identification of Molecules Which Interact with CKSR

CKSR, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled CKSR, washed, and any wells with labeled CKSR complex are assayed. Data obtained using different concentrations of CKSR are used to calculate values for the number, affinity, and association of CKSR with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Program | Description | Reference | Parameter Threshold |
|---|---|---|---|
| ABI FACTURA | A program that removes vector sequences and masks ambiguous bases in nucleic acid sequences. | Perkin-Elmer Applied Biosystems, Foster City, CA. | |
| ABI/ PARACEL FDF | A Fast Data Finder useful in comparing and annotating amino acid or nucleic acid sequences. | Perkin-Elmer Applied Biosystems, Foster City, CA; Paracel Inc., Pasadena, CA. | Mismatch <50% |
| ABI AutoAssembler | A program that assembles nucleic acid sequences. | Perkin-Elmer Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S.F. et al. (1990) J. Mol. Biol. 215:403–410; Altschul, S.F. et al. (1997) Nucleic Acids Res. 25: 3389–3402. | ESTs: Probability value = 1.0E−8 or less Full Length sequences: Probability value = 1.0E−10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. 85:2444–2448; Pearson, W. R. (1990) Methods Enzymol. 183: 63–98; and Smith, T. F. and M. S. Waterman (1981) Adv. Appl. Math. 2:482–489. | ESTs: fasta E value = 1.06E−6 Assembled ESTs: fasta Identity = 95% or greater and Match length = 200 bases or greater; fastx E value = 1.0E−8 or less Full Length sequences: fastx score = 100 or greater |
| BLIMPS | A BLocks IMProved Searcher that matches a sequence against those in BLOCKS and PRINTS databases to search for gene families, sequence homology, and structural fingerprint regions. | Henikoff, S and J. G. Henikoff, Nucl. Acid Res., 19:6565–72, 1991. J. G. Henikoff and S. Henikoff(1996) Methods Enzymol. 266:88–105; and Attwood, T. K. et al. (1997) J. Chem. Inf. Comput. Sci. 37: 417–424. | Score = 1000 or greater; Ratio of Score/Strength = 0.75 or larger; and Probability value = 1.0E−3 or less |
| PFAM | A Hidden Markov Models-based application useful for protein family search. | Krogh, A. et al. (1994) J. Mol. Biol., 235:1501–1531; Sonnhammer, E.L.L. et al. (1988) Nucleic Acids Res. 26:320–322. | Score = 10–50 bits, depending on individual protein families |
| ProfileScan | An algorithm that searches for structural and sequence motifs in protein sequences that match sequence patterns defined in Prosite. | Gribskov, M. et al. (1988) CABIOS 4:61–66; Gribskov, et al. (1989) Methods Enzymol. 183:146–159; Bairoch, A. et al. (1997) Nucleic Acids Res. 25: 217–221. | Score = 4.0 or greater |
| Phred | A base-calling algorithm that examines automated sequencer traces with high sensitivity and probability. | Ewing, B. et al. (1998) Genome Res. 8:175–185; Ewing, B. and P. Green (1998) Genome Res. 8:186–194. | |
| Phrap | A Phils Revised Assembly Program including SWAT and CrossMatch, programs based on efficient implementation of the Smith-Waterwan algorithm, useful in searching sequence homology and assembling DNA sequences. | Smith, T.F. and M. S. Waterman (1981) Adv. Appl. Math. 2:482–489; Smith, T.F. and M. S. Waterman (1981) J. Mol. Biol. 147:195–197; and Green, P., University of Washington, Seattle, WA. | Score = 120 or greater; Match length = 56 or greater |
| Consed | A graphical tool for viewing and editing Phrap assemblies | Gordon, D. et al. (1998) Genome Res. 8:195–202. | |

TABLE 1-continued

| Program | Description | Reference | Parameter Threshold |
|---------|-------------|-----------|---------------------|
| SPScan | A weight matrix analysis program that scans protein sequences for the presence of secretory signal peptides. | Nielson, H. et al. (1997) Protein Engineering 10:1–6; Claverie, J. M. and S. Audic (1997) CABIOS 12: 431–439. | Score = 5 or greater |
| Motifs | A program that searches amino acid sequences for patterns that matched those defined in Prosite. | Bairoch et al. supra; Wisconsin Package Program Manual, version 9, page M51–59, Genetics Computer Group, Madison, WI. | |

What is claimed is:

1. A purified polypeptide comprising an amino acid sequence selected from the group consisting of:
   a) an amino acid sequence of SEQ ID NO:1 or SEQ ID NO:2,
   b) a naturally-occurring biologically active amino acid sequence having at least 90% sequence identity to the sequence of (a)
      wherein said biologically active fragment induces growth arrest when expressed at elevated levels in a mammalian cell line
   c) a biologically-active fragment of the amino acid sequence of (a),
   wherein said biologically active fragment induces growth arrest when expressed at elevated levels in a mammilian cell line.

2. An isolated polypeptide of claim 1, having a sequence of SEQ ID NO:1 or SEQ ID NO:2.

3. A pharmaceutical composition comprising a polypeptide of claim 1 and a pharmaceutically acceptable excipient.

4. A pharmaceutical composition of claim 3, wherein the polypeptide has the sequence of SEQ ID NO:1 or SEQ ID NO:2.

* * * * *

UNITED STATES PATENT AND TRADEMARK OFFICE
CERTIFICATE OF CORRECTION

PATENT NO. : 6,201,106 B1
DATED : March 12, 2001
INVENTOR(S) : Henry Yue, Neil C. Corley, Karl J. Guegler, Mariah R. Baughn Page 1 of 1

It is certified that error appears in the above-identified patent and that said Letters Patent is hereby corrected as shown below:

Column 53, claim 1,
Line 38-40, delete starting from " fragment induces" and ending " cell line" and insert -- amino acid sequence induces growth arrest when expressed at elevated levels in a mammalian cell line, and --;

Column 54, claim 3,
Line 35, delete " pharmaceutical";

Column 54, claim 4,
Line 37, delete " pharmaceutical".

Signed and Sealed this

Twenty-eighth Day of August, 2001

Attest:

*Nicholas P. Godici*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,201,106 B1  Page 1 of 1
DATED : March 13, 2001
INVENTOR(S) : Henry Yue, Neil C. Corley, Karl J. Guegler and Mariah R. Baughn It is certified that error appears in the above-identified patent and that said Letters Patent is hereby corrected as shown below:

Column 53, claim 1,
Line 38-40, delete starting from " fragment induces" and ending " cell line"
and insert -- amino acid sequence induces growth arrest when expressed at elevated levels in a mammalian cell line, and --;

Column 54, claim 3,
Line 35, delete " pharmaceutical";

Column 54, claim 4,
Line 37, delete " pharmaceutical".

This certificate supersedes Certificate of Correction issued August 28, 2001.

Signed and Sealed this

Twentieth Day of August, 2002

Attest:

Attesting Officer

JAMES E. ROGAN
Director of the United States Patent and Trademark Office

SEQUENCE LISTING

<160> NUMBER OF SEQ ID NOS: 6

<210> SEQ ID NO 1
<211> LENGTH: 476
<212> TYPE: PRT
<213> ORGANISM: Homo sapiens
<220> FEATURE: -
<223> OTHER INFORMATION: 2280326

<400> SEQUENCE: 1

```
Met Ala Ser Phe Leu Ser Arg Thr Arg Glu Gln Ser Gln Leu Pro
 1               5                  10                  15

Arg Pro Trp Leu Pro Leu Leu Gly Gly Ile Gly Gly Trp Ala Pro
                20                  25                  30

Lys Trp Ala Pro Gly Phe Pro Leu Pro Leu Gly Arg Gly Gln Arg
                35                  40                  45

Asp Thr Gly Ser Gly Ser Arg Thr Asp Phe Leu Leu Ser Arg Asn
                50                  55                  60

Glu His Ala Cys Pro Leu Gln Ala Gly Leu Gly Leu Thr Gln Arg
                65                  70                  75

Lys Pro Lys Ala Ile Arg Gly Arg Glu Gly Arg Ala Thr Asn Gln
                80                  85                  90

Gly Gln Gly Glu Thr Gln Asn Glu Arg Ala Pro Trp Gly Ala Arg
                95                 100                 105

Gln Arg Leu Gly Val Met Ala Glu Leu Gln Gln Leu Gln Glu Phe
               110                 115                 120

Glu Ile Pro Thr Gly Arg Glu Ala Leu Arg Gly Asn His Ser Ala
               125                 130                 135

Leu Leu Arg Val Ala Asp Tyr Cys Glu Asp Asn Tyr Val Gln Ala
               140                 145                 150

Thr Asp Lys Arg Lys Ala Leu Glu Glu Thr Met Ala Phe Thr Thr
               155                 160                 165

Gln Ala Leu Ala Ser Val Ala Tyr Gln Val Gly Asn Leu Ala Gly
               170                 175                 180

His Thr Leu Arg Met Leu Asp Leu Gln Gly Ala Ala Leu Arg Gln
               185                 190                 195

Val Glu Ala Arg Val Ser Thr Leu Gly Gln Met Val Asn Met His
               200                 205                 210

Met Glu Lys Val Ala Arg Arg Glu Ile Gly Thr Leu Ala Thr Val
               215                 220                 225

Gln Arg Leu Pro Pro Gly Gln Lys Val Ile Ala Pro Glu Asn Leu
               230                 235                 240

Pro Pro Leu Thr Pro Tyr Cys Arg Arg Pro Leu Asn Phe Gly Cys
               245                 250                 255
```

```
Leu Asp Asp Ile Gly His Gly Ile Lys Asp Leu Ser Thr Gln Leu
                260                 265                 270

Ser Arg Thr Gly Thr Leu Ser Arg Lys Ser Ile Lys Ala Pro Ala
                275                 280                 285

Thr Pro Ala Ser Ala Thr Leu Gly Arg Pro Pro Arg Ile Pro Glu
                290                 295                 300

Pro Val His Leu Pro Val Val Pro Asp Gly Arg Leu Ser Ala Ala
                305                 310                 315

Ser Ser Ala Ser Ser Leu Ala Ser Ala Gly Ser Ala Glu Gly Val
                320                 325                 330

Gly Gly Ala Pro Thr Pro Lys Gly Gln Ala Ala Pro Pro Ala Pro
                335                 340                 345

Pro Leu Pro Ser Ser Leu Asp Pro Pro Pro Pro Ala Ala Val
                350                 355                 360

Glu Val Phe Gln Arg Pro Pro Thr Leu Glu Glu Leu Ser Pro Pro
                365                 370                 375

Pro Pro Asp Glu Glu Leu Pro Leu Pro Leu Asp Leu Pro Pro Pro
                380                 385                 390

Pro Pro Leu Asp Gly Asp Glu Leu Gly Leu Pro Pro Pro Pro Pro
                395                 400                 405

Gly Phe Gly Pro Asp Glu Pro Ser Trp Val Pro Ala Ser Tyr Leu
                410                 415                 420

Glu Lys Val Val Thr Leu Tyr Pro Tyr Thr Ser Gln Lys Asp Asn
                425                 430                 435

Glu Leu Ser Phe Ser Glu Gly Thr Val Ile Cys Val Thr Arg Arg
                440                 445                 450

Tyr Ser Asp Gly Trp Cys Glu Gly Val Ser Ser Glu Gly Thr Gly
                455                 460                 465

Phe Phe Pro Gly Asn Tyr Val Glu Pro Ser Cys
                470                 475

<210> SEQ ID NO 2
<211> LENGTH: 170
<212> TYPE: PRT
<213> ORGANISM: Homo sapiens
<220> FEATURE: -
<223> OTHER INFORMATION: 2462908

<400> SEQUENCE: 2

Met Pro Val Pro Ala Ser Trp Pro His Pro Pro Asp Pro Phe Leu
  1               5                  10                  15

Leu Leu Thr Leu Leu Leu Gly Leu Thr Glu Val Ala Gly Glu Glu
                 20                  25                  30

Glu Leu Gln Met Ile Gln Pro Glu Lys Leu Leu Leu Val Thr Val
                 35                  40                  45

Gly Lys Thr Ala Thr Leu His Cys Thr Val Thr Ser Leu Leu Pro
                 50                  55                  60

Val Gly Pro Val Leu Trp Phe Arg Gly Val Gly Pro Gly Arg Glu
                 65                  70                  75

Leu Ile Tyr Asn Gln Lys Glu Gly His Phe Pro Arg Val Thr Thr
                 80                  85                  90

Val Ser Asp Leu Thr Lys Arg Asn Asn Met Asp Phe Ser Ile Arg
                 95                 100                 105

Ile Ser Ser Ile Thr Pro Ala Asp Val Gly Thr Tyr Tyr Cys Val
                110                 115                 120
```

```
Lys Phe Arg Lys Gly Ser Pro Glu Asn Val Glu Phe Lys Ser Gly
            125                 130                 135

Pro Gly Thr Glu Met Ala Leu Gly Gly Pro Ala Ser Ser Leu Thr
            140                 145                 150

Ala Leu Leu Leu Ile Ala Val Leu Leu Gly Pro Ile Tyr Val Pro
            155                 160                 165

Trp Lys Gln Lys Thr
            170

<210> SEQ ID NO 3
<211> LENGTH: 2295
<212> TYPE: DNA
<213> ORGANISM: Homo sapiens
<220> FEATURE: -
<223> OTHER INFORMATION: 2280326

<400> SEQUENCE: 3
ccacctccat cttcaacagg tccttctcgc tgagatcctg ggccatcctg ccctagacag     60
acctgatcct gccacagaag agcacactct ccaagtcact tgtcctggac tcaggtaaga    120
tagtgtttga gcctcctagt tcttcatcag ctgaaaatct tcagataaag cagatggcca    180
gtttcctctc caggaccagg gagcaatcac agctgccccg accttggctt cctctgctgg    240
gtgggattgg gggctgggcc cccaaatggg cccctggctt ccccccttcct ctgggcaggg    300
gacagagaga cacaggctcg gggagcagga ctgacttcct cttgtcccgg aatgagcatg    360
cctgcccttt gcaagcaggt ttgggtctca cgcagaggaa accaaaagca ataagaggga    420
gggaaggcag agcaaccaat caagggcagg gtgagactca aaacgagcgg gctccctggg    480
gagccagaca gaggctgggg gtgatggcgg agctacagca gctgcaggag tttgagatcc    540
ccactggccg ggaggctctg aggggcaacc acagtgccct gctgcgggtc gctgactact    600
gcgaggacaa ctatgtgcag gccacagaca gcggaaggc gctggaggag accatggcct    660
tcactaccca ggcactggcc agcgtggcct accaggtggg caacctggcc gggcacactc    720
tgcgcatgtt ggacctgcag ggggccgccc tgcggcaggt ggaagcccgt gtaagcacgc    780
tgggccagat ggtgaacatg catatggaga aggtggcccg aagggagatc ggcaccttag    840
ccactgtcca gcggctgccc cccggccaga aggtcatcgc cccagagaac ctaccccctc    900
tcacgcccta ctgcaggaga cccctcaact ttggctgcct ggacgacatt ggccatggga    960
tcaaggacct cagcacgcag ctgtcaagaa caggcaccct gtctcgaaag agcatcaagg   1020
cccctgccac acccgcctcc gccaccttgg ggagaccacc ccggattccc gagccagtgc   1080
acctgccggt ggtgcccgac ggcagactct ccgccgcctc tctgcgtctc tccctggcct   1140
cggccggcag cgccgaaggt gtcggtgggg cccccacgcc caaggggcag gcagcacctc   1200
cagccccacc tctccccagc tccttggacc cacctcctcc accagcagcc gtcgaggtgt   1260
tccagcggcc tcccacgctg gaggagttgt ccccaccccc accggacgaa gagctgcccc   1320
tgccactgga cctgcctcct cctccacccc tggatggaga tgaattgggg ctgcctccac   1380
ccccaccagg atttgggcct gatgagccca gctgggtgcc tgcctcatac ttggagaaag   1440
tggtgacact gtaccatac accagccaga aggacaatga gctctccttc tctgagggca   1500
ctgtcatctg tgtcactcgc cgctactccg atggctggtg cgagggcgtc agctcagagg   1560
ggactggatt cttccctggg aactatgtgg agcccagctg ctgacagccc agggctctct   1620
gggcagctga tgtctgcact gagtgggttt catgagcccc aagccaaaac cagctccagt   1680
```

```
cacagctgga ctgggtctgc ccacctcttg ggctgtgagc tgtgttctgt ccttcctccc    1740
atcggaggga gaagggtcc tggggagaga gaatttatcc agaggcctgc tgcagatggg     1800
gaagagctgg aaaccaagaa gtttgtcaac agaggacccc tactccatgc aggacagggt    1860
ctcctgctgc aagtcccaac tttgaataaa acagatgatg tcctgtgact gccccacaga    1920
gataaggggc caggagggat tgaaaggcat cccagttcta aggctgctgc taattacagc    1980
ccccaacctc caacccacca gctgacctag aagcagcatc ttcccatttc ctcagtaccc    2040
acaaagtgca gcccacattg gaccccagac acccctctgc agccattgac tgcaacttgt    2100
tcttttgccc attgcttgct gtgtgtgtgg tgtgttcata tgtggctggg cacttgccca    2160
agagtgggaa cgatctccat gacttaagcg gggctctccg agagcacctc actgtcaact    2220
ctgagactgt cgcgagagag atctcagtca tttcttcccc cttcacctcc tttatagttg    2280
taaaactcca gagga                                                     2295

<210> SEQ ID NO 4
<211> LENGTH: 1022
<212> TYPE: DNA
<213> ORGANISM: Homo sapiens
<220> FEATURE: -
<223> OTHER INFORMATION: 2462908

<400> SEQUENCE: 4
cagagcaggc ttctgaggtc tccaaaatgc ctgtcccagc ctcctggccc catcctcctg      60
atcctttcct gcttctgact ctactgctgg gacttacaga agtggcaggt gaggaggagc     120
tacagatgat tcagcctgag aagctcctgt tggtcacagt tggaaagaca gccactctgc     180
actgcactgt gacctccctg cttcccgtgg gacccgtcct gtggttcaga ggagttggac     240
caggccgaga attaatctac aatcaaaaag aaggccactt ccccagggta caacagtttt     300
cagacctcac aaagagaaac aacatggact tttccatccg catcagtagc atcaccccag     360
cagatgtcgg cacatactac tgtgtgaagt tcgaaaagg gagccctgag aacgtggagt      420
ttaagtctgg accaggcact gagatggctt tgggtggccc ggcatcatcc ttactgcgc      480 tgctcctcat agctgtcctc ctgggcccca tctacgtccc ctggaagcag aagacctgac     540
tctccttcct tcctccccctg ccacgtggga ccctcatctc tgctgcctcc ttcctttcct    600
gagaggctca gcttgagaga atgagccagt gagaagcttc tctagacttg gctccaaaca     660
tctcccctcc caagacatct gcctgcccac aggctcctgt tgctccttca cacagacctg    720
gatgccccag agcaaggtct tcattcatgg tcctgagcag gtgccatggg attgggctct    780
gggcactgac ttaacggcac ctccctagaa ggcgagaaac atgccaaatc taaacacacc   840
aggactccca tccatcgcct tgagactgac cgtaaaccac agacgctctc caggttctca   900
agagttatcc tgccttccag attcctgcct atcccaactc cccagccttg ttgaggttct   960
ctattgcctc ttgaatacaa atgcactccc aaagtggttt taagaaaata aaagattat   1020 cc                                                                 1022

<210> SEQ ID NO 5
<211> LENGTH: 480
<212> TYPE: PRT
<213> ORGANISM: Homo sapiens
<220> FEATURE: -
<223> OTHER INFORMATION: g2245671

<400> SEQUENCE: 5
```

-continued

```
Met Ala Glu Leu Gln Met Leu Glu Glu Ile Pro Ser Gly
 1               5                  10                  15

Lys Arg Ala Leu Ile Glu Ser Tyr Gln Asn Leu Thr Arg Val Ala
                 20                  25                  30

Asp Tyr Cys Glu Asn Asn Tyr Ile Gln Ala Thr Asp Lys Arg Lys
                 35                  40                  45

Ala Leu Glu Glu Thr Lys Ala Tyr Thr Thr Gln Ser Leu Ala Ser
                 50                  55                  60

Val Ala Tyr Gln Ile Asn Ala Leu Ala Asn Asn Val Leu Gln Leu
                 65                  70                  75

Leu Asp Ile Gln Ala Ser Gln Leu Arg Arg Met Glu Ser Ser Ile
                 80                  85                  90

Asn His Ile Ser Gln Thr Val Asp Ile His Lys Glu Lys Val Ala
                 95                 100                 105

Arg Arg Glu Ile Gly Ile Leu Thr Thr Asn Lys Asn Thr Ser Arg
                110                 115                 120

Thr His Lys Ile Ile Ala Pro Ala Asn Met Glu Arg Pro Val Arg
                125                 130                 135

Tyr Ile Arg Lys Pro Ile Asp Tyr Thr Val Leu Asp Asp Val Gly
                140                 145                 150

His Gly Val Lys Trp Leu Lys Ala Lys His Gly Asn Asn Gln Pro
                155                 160                 165

Ala Arg Thr Gly Thr Leu Ser Arg Thr Asn Pro Pro Thr Gln Lys
                170                 175                 180

Pro Pro Ser Pro Pro Met Ser Gly Arg Gly Thr Leu Gly Arg Asn
                185                 190                 195

Thr Pro Tyr Lys Thr Leu Glu Pro Val Lys Pro Pro Thr Val Pro
                200                 205                 210

Asn Asp Tyr Met Thr Ser Pro Ala Arg Leu Gly Ser Gln His Ser
                215                 220                 225

Pro Gly Arg Thr Ala Ser Leu Asn Gln Arg Pro Arg Thr His Ser
                230                 235                 240

Gly Ser Ser Gly Gly Ser Gly Ser Arg Glu Asn Ser Gly Ser Ser
                245                 250                 255

Ser Ile Gly Ile Pro Ile Ala Val Pro Thr Pro Ser Pro Pro Thr
                260                 265                 270

Ile Gly Pro Ala Pro Gly Ser Ala Pro Gly Ser Gln Tyr Gly Thr
                275                 280                 285

Met Thr Arg Gln Ile Ser Arg His Asn Ser Thr Thr Ser Ser Thr
                290                 295                 300

Ser Ser Gly Gly Tyr Arg Arg Thr Pro Ser Val Thr Ala Gln Phe
                305                 310                 315

Ser Ala Gln Pro His Val Asn Gly Gly Pro Leu Tyr Ser Gln Asn
                320                 325                 330

Ser Ile Ser Ile Ala Pro Pro Pro Pro Met Pro Gln Leu Thr
                335                 340                 345

Pro Gln Ile Pro Leu Thr Gly Phe Val Ala Arg Val Gln Glu Asn
                350                 355                 360

Ile Ala Asp Ser Pro Thr Pro Pro Pro Pro Pro Asp Asp
                365                 370                 375

Ile Pro Met Phe Asp Asp Ser Pro Pro Pro Pro Pro Pro
                380                 385                 390
```

-continued

```
Val Asp Tyr Glu Asp Glu Ala Ala Val Val Gln Tyr Asn Asp
            395                 400                 405

Pro Tyr Ala Asp Gly Asp Pro Ala Trp Ala Pro Lys Asn Tyr Ile
            410                 415                 420

Glu Lys Val Val Ala Ile Tyr Asp Tyr Thr Lys Asp Lys Asp Asp
            425                 430                 435

Glu Leu Ser Phe Met Glu Gly Ala Ile Ile Tyr Val Ile Lys Lys
            440                 445                 450

Asn Asp Asp Gly Trp Tyr Glu Gly Val Cys Asn Arg Val Thr Gly
            455                 460                 465

Leu Phe Pro Gly Asn Tyr Val Glu Ser Ile Met His Tyr Thr Asp
            470                 475                 480

<210> SEQ ID NO 6
<211> LENGTH: 398
<212> TYPE: PRT
<213> ORGANISM: Homo sapiens
<220> FEATURE: -
<223> OTHER INFORMATION: g2052058

<400> SEQUENCE: 6

Met Pro Val Pro Ala Ser Trp Pro His Leu Pro Ser Pro Phe Leu
 1               5                  10                  15

Leu Met Thr Leu Leu Leu Gly Arg Leu Thr Gly Val Ala Gly Glu
            20                  25                  30

Asp Glu Leu Gln Val Ile Gln Pro Glu Lys Ser Val Ser Val Ala
            35                  40                  45

Ala Gly Glu Ser Ala Thr Leu Arg Cys Ala Met Thr Ser Leu Ile
            50                  55                  60

Pro Val Gly Pro Ile Met Trp Phe Arg Gly Ala Gly Ala Gly Arg
            65                  70                  75

Glu Leu Ile Tyr Asn Gln Lys Glu Gly His Phe Pro Arg Val Thr
            80                  85                  90

Thr Val Ser Glu Leu Thr Lys Arg Asn Asn Leu Asn Phe Ser Ile
            95                  100                 105

Ser Ile Ser Asn Ile Thr Pro Ala Asp Ala Gly Thr Tyr Tyr Cys
            110                 115                 120

Val Lys Phe Arg Lys Gly Ser Pro Asp Val Glu Phe Lys Ser
            125                 130                 135

Gly Ala Gly Thr Glu Leu Ser Val Arg Ala Lys Pro Ser Ala Pro
            140                 145                 150

Val Val Ser Gly Pro Ala Val Arg Ala Thr Pro Glu His Thr Val
            155                 160                 165

Ser Phe Thr Cys Glu Ser His Gly Phe Ser Pro Arg Asp Ile Thr
            170                 175                 180

Leu Lys Trp Phe Lys Asn Gly Asn Glu Leu Ser Asp Phe Gln Thr
            185                 190                 195

Asn Val Asp Pro Ala Gly Asp Ser Val Ser Tyr Ser Ile His Ser
            200                 205                 210

Thr Ala Arg Val Val Leu Thr Arg Gly Asp Val His Ser Gln Val
            215                 220                 225

Ile Cys Glu Met Ala His Ile Thr Leu Gln Gly Asp Pro Leu Arg
            230                 235                 240

Gly Thr Ala Asn Leu Ser Glu Ala Ile Arg Val Pro Pro Thr Leu
            245                 250                 255
```

```
                                         -continued

Glu Val Thr Gln Gln Pro Met Arg Ala Glu Asn Gln Ala Asn Val
                260                 265                 270

Thr Cys Gln Val Ser Asn Phe Tyr Pro Arg Gly Leu Gln Leu Thr
                275                 280                 285

Trp Leu Glu Asn Gly Asn Val Ser Arg Thr Glu Thr Ala Ser Thr
                290                 295                 300

Leu Ile Glu Asn Lys Asp Gly Thr Tyr Asn Trp Met Ser Trp Leu
                305                 310                 315

Leu Val Asn Thr Cys Ala His Arg Asp Asp Val Val Leu Thr Cys
                320                 325                 330

Gln Val Glu His Asp Gly Gln Gln Ala Val Ser Lys Ser Tyr Ala
                335                 340                 345

Leu Glu Ile Ser Ala His Gln Lys Glu His Gly Ser Asp Ile Thr
                350                 355                 360

His Glu Pro Ala Leu Ala Pro Thr Ala Pro Leu Leu Val Ala Leu
                365                 370                 375

Leu Leu Gly Pro Lys Leu Leu Leu Val Val Gly Val Ser Ala Ile
                380                 385                 390

Tyr Ile Cys Trp Lys Gln Lys Ala
                395
```